(12) United States Patent
Cho et al.

(10) Patent No.: US 10,363,440 B2
(45) Date of Patent: Jul. 30, 2019

(54) LINE-FOCUSED ULTRASOUND TRANSDUCER AND HIGH-INTENSITY LINE FOCUSED ULTRASOUND GENERATOR INCLUDING SAME

(71) Applicant: KORUST CO., LTD., Anyang-si, Gyeonggi-do (KR)

(72) Inventors: Sung-Chan Cho, Seongnam-si (KR); Min-Joo Choi, Jeju-si (KR)

(73) Assignee: KORUST CO., LTD., Anyang-si, Gyeonggi-Do (KR)

( * ) Notice: Subject to any disclaimer, the term of this patent is extended or adjusted under 35 U.S.C. 154(b) by 848 days.

(21) Appl. No.: 14/770,022

(22) PCT Filed: Dec. 6, 2013

(86) PCT No.: PCT/KR2013/011279
§ 371 (c)(1),
(2) Date: Aug. 24, 2015

(87) PCT Pub. No.: WO2014/129732
PCT Pub. Date: Aug. 28, 2014

(65) Prior Publication Data
US 2016/0001097 A1    Jan. 7, 2016

(30) Foreign Application Priority Data

Feb. 25, 2013 (KR) .................. 10-2013-0019764

(51) Int. Cl.
*A61B 8/00* (2006.01)
*A61N 7/02* (2006.01)
(Continued)

(52) U.S. Cl.
CPC .................. *A61N 7/02* (2013.01); *A61B 8/00* (2013.01); *A61B 8/44* (2013.01);
(Continued)

(58) Field of Classification Search
CPC .............. A61N 7/02; A61N 2007/0065; A61N 2007/0091; A61B 8/00; A61B 8/44; G01S 7/52079
See application file for complete search history.

(56) References Cited

U.S. PATENT DOCUMENTS 5,471,988 A * 12/1995 Fujio ........................ A61B 8/12
600/439
5,560,362 A * 10/1996 Sliwa, Jr. ............... A61B 8/546
600/439
(Continued)

FOREIGN PATENT DOCUMENTS

CN        1754586 A     4/2006
CN      102112059 A     6/2011
(Continued)

*Primary Examiner* — Peter Luong
(74) *Attorney, Agent, or Firm* — Rabin & Berdo, P.C.

(57) ABSTRACT

The present invention has been made in an effort to provide a line-focused ultrasound transducer and a high intensity line-focused ultrasound generation device including the same in which ultrasound is focused in a line so that the treatment time can be reduced and the structure can be simplified. A line-focused ultrasound transducer which focuses in a line shape includes: a therapeutic piezoelectric member having a hollow semi-cylindrical shape; a first electrode portion which is provided on an inner surface of the therapeutic piezoelectric member; and a second electrode portion which is provided on an outer surface of the therapeutic piezoelectric member in correspondence with the first electrode portion.

5 Claims, 21 Drawing Sheets

(51) Int. Cl.
 *G01S 7/52* (2006.01)
 *A61N 7/00* (2006.01)
(52) U.S. Cl.
 CPC .............. *A61N 2007/0065* (2013.01); *A61N 2007/0091* (2013.01); *G01S 7/52079* (2013.01)

(56) References Cited

U.S. PATENT DOCUMENTS

| | | | | |
|---|---|---|---|---|
| 5,844,140 A | * | 12/1998 | Seale | A61B 8/08 |
| | | | | 600/443 |
| 6,786,870 B2 | * | 9/2004 | Miyaki | A61B 8/0833 |
| | | | | 600/443 |
| 7,891,230 B2 | * | 2/2011 | Randall | A61B 8/00 |
| | | | | 73/1.82 |
| 9,570,842 B2 | * | 2/2017 | Nordgren | H01R 13/6205 |
| 2001/0031922 A1 | * | 10/2001 | Weng | A61B 17/0057 |
| | | | | 600/439 |
| 2003/0206613 A1 | * | 11/2003 | Collins | A61N 5/1049 |
| | | | | 378/84 |
| 2006/0184072 A1 | | 8/2006 | Manna | |
| 2009/0230822 A1 | | 9/2009 | Kushculey et al. | |
| 2009/0240148 A1 | * | 9/2009 | Jeong | A61B 8/4483 |
| | | | | 600/439 |
| 2013/0131704 A1 | | 5/2013 | Pechoux | |

FOREIGN PATENT DOCUMENTS

| | | |
|---|---|---|
| JP | 2008-522783 A | 7/2008 |
| JP | 2009-247683 A | 10/2009 |
| KR | 10-2012-0101661 A | 9/2012 |
| KR | 10-2012-0128277 A | 11/2012 |

* cited by examiner

[FIG. 1]
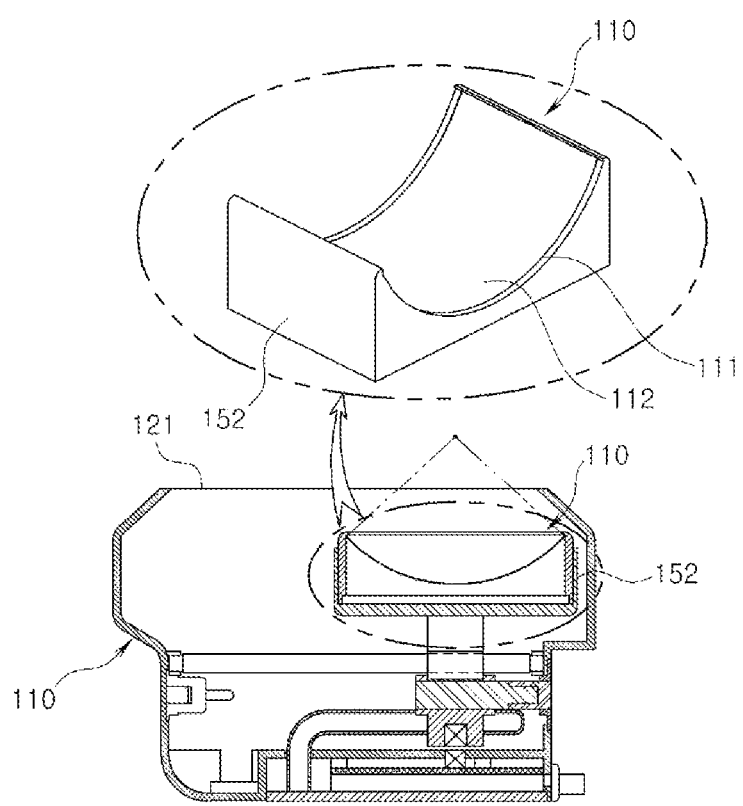

[FIG. 2]
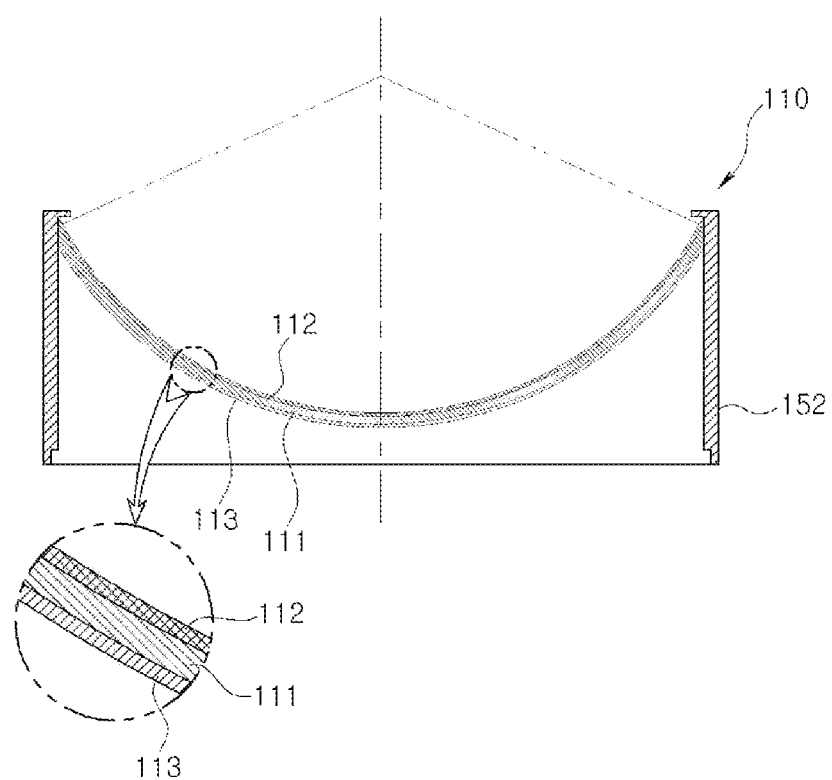

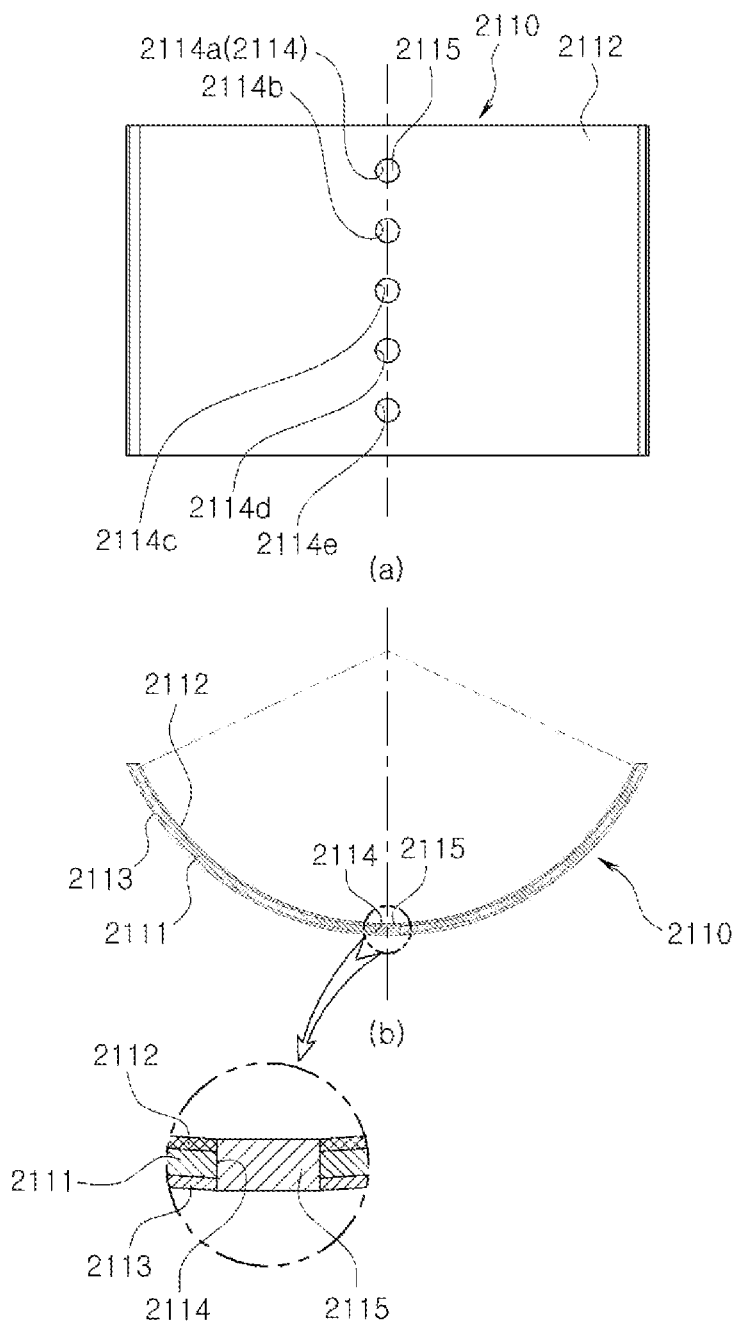
[FIG. 3]

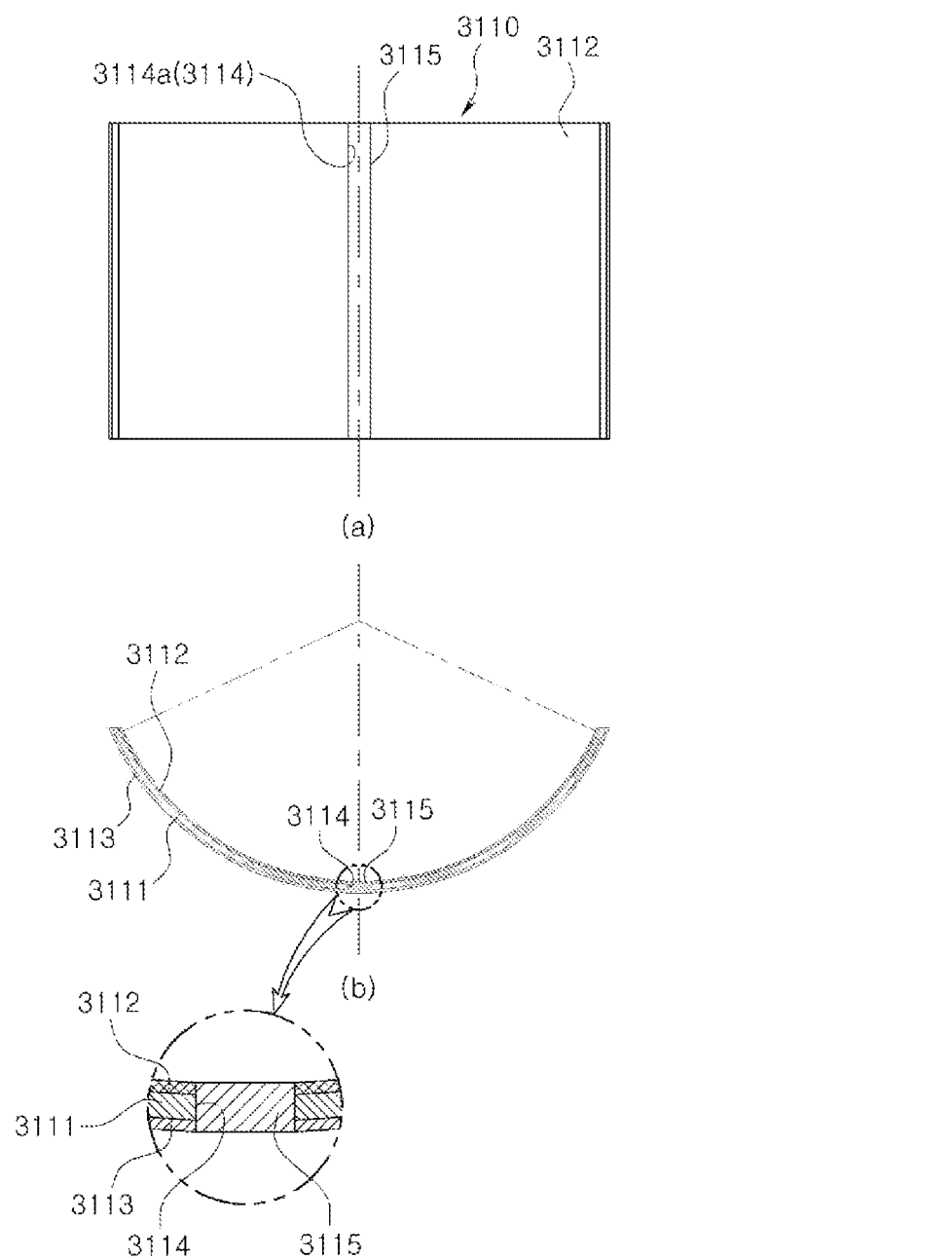
[FIG. 4]

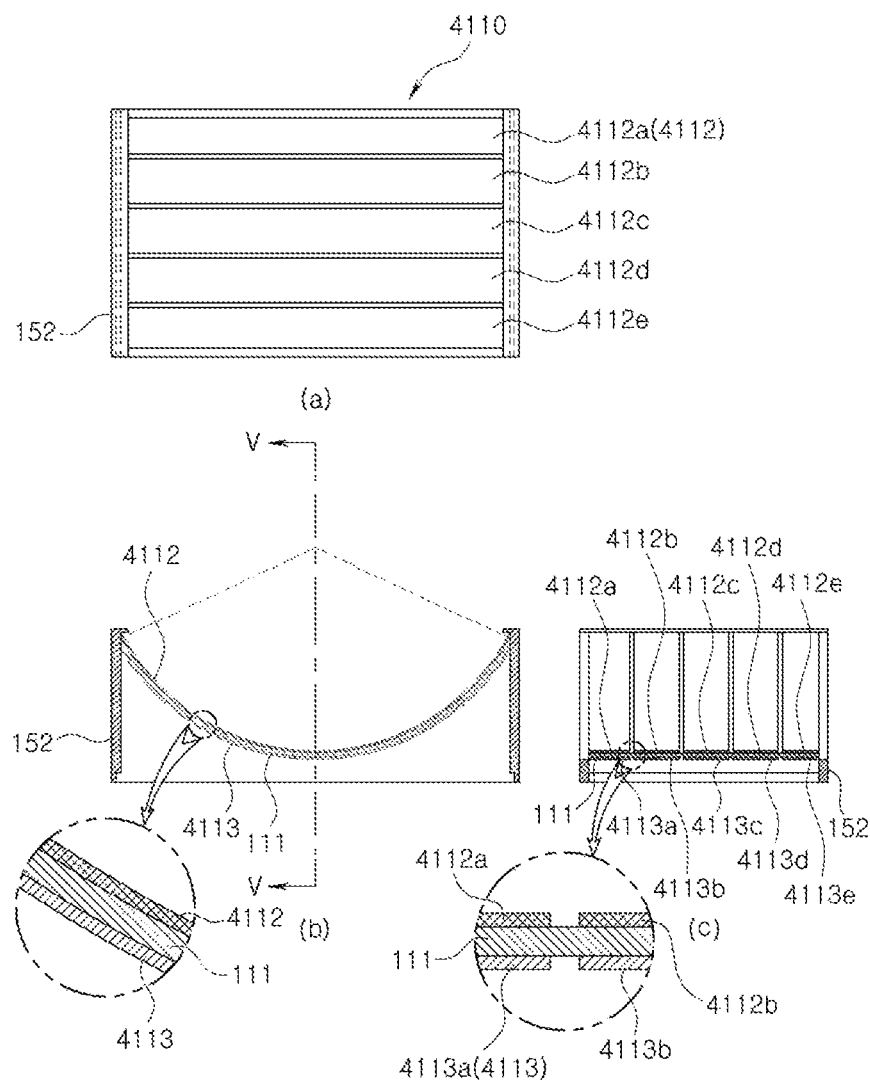
[FIG. 5]

[FIG. 6]
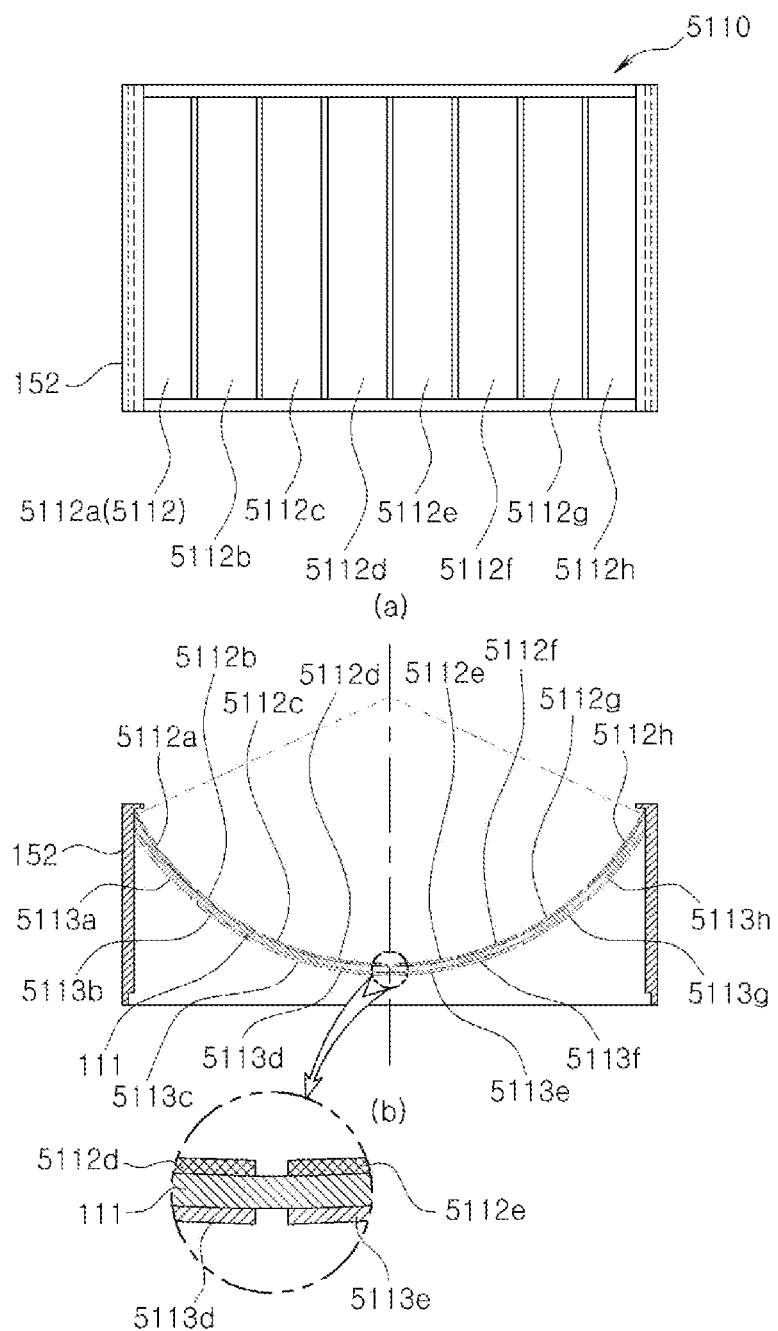

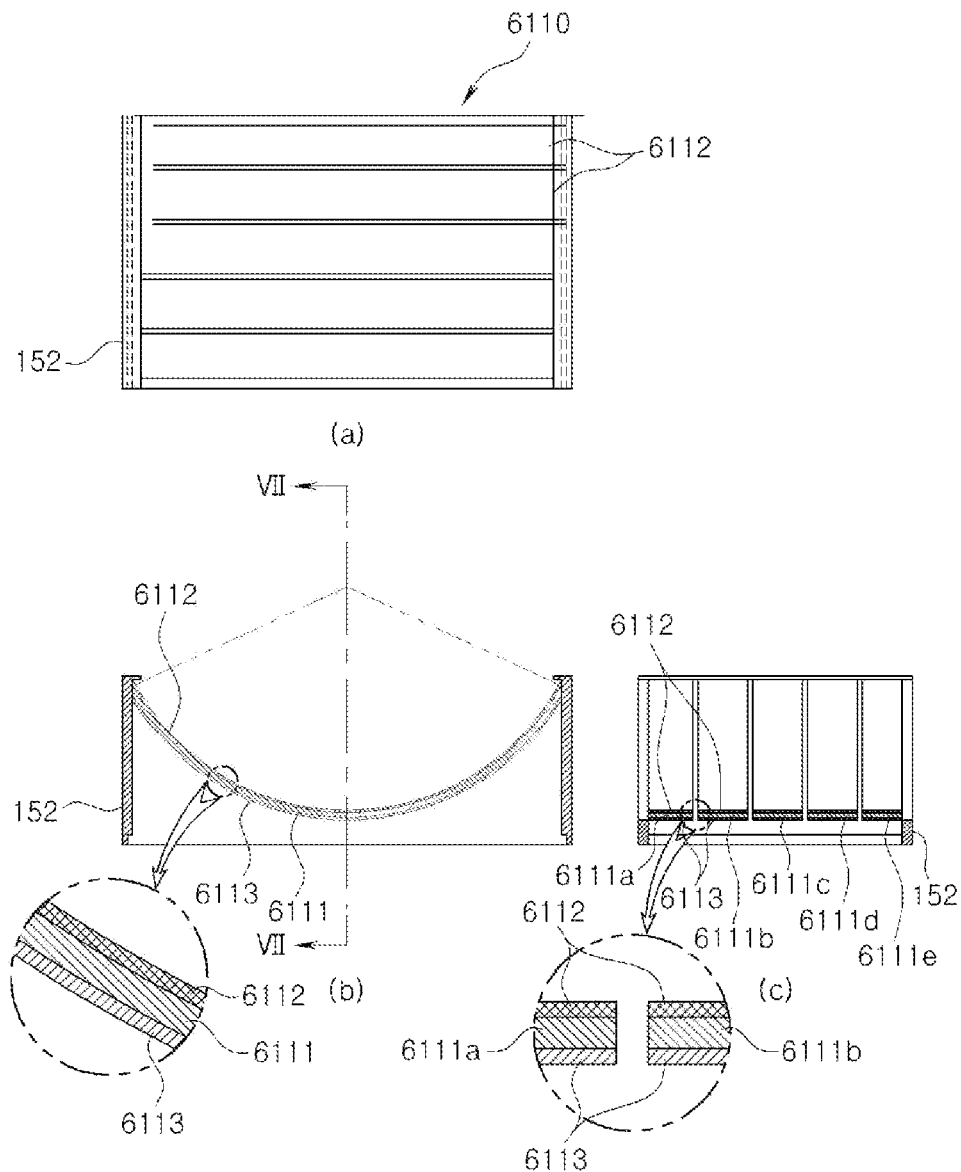
[FIG. 7]

[FIG. 8]
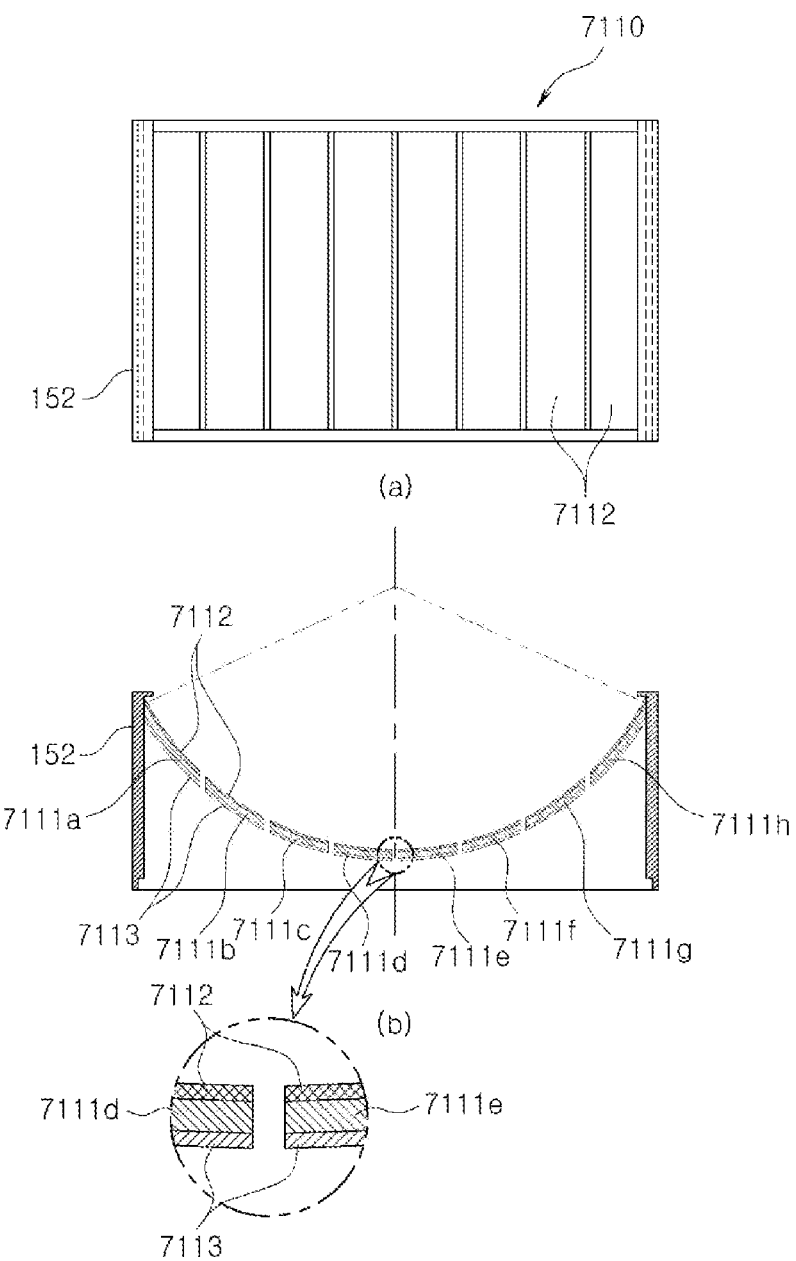

[FIG. 9]
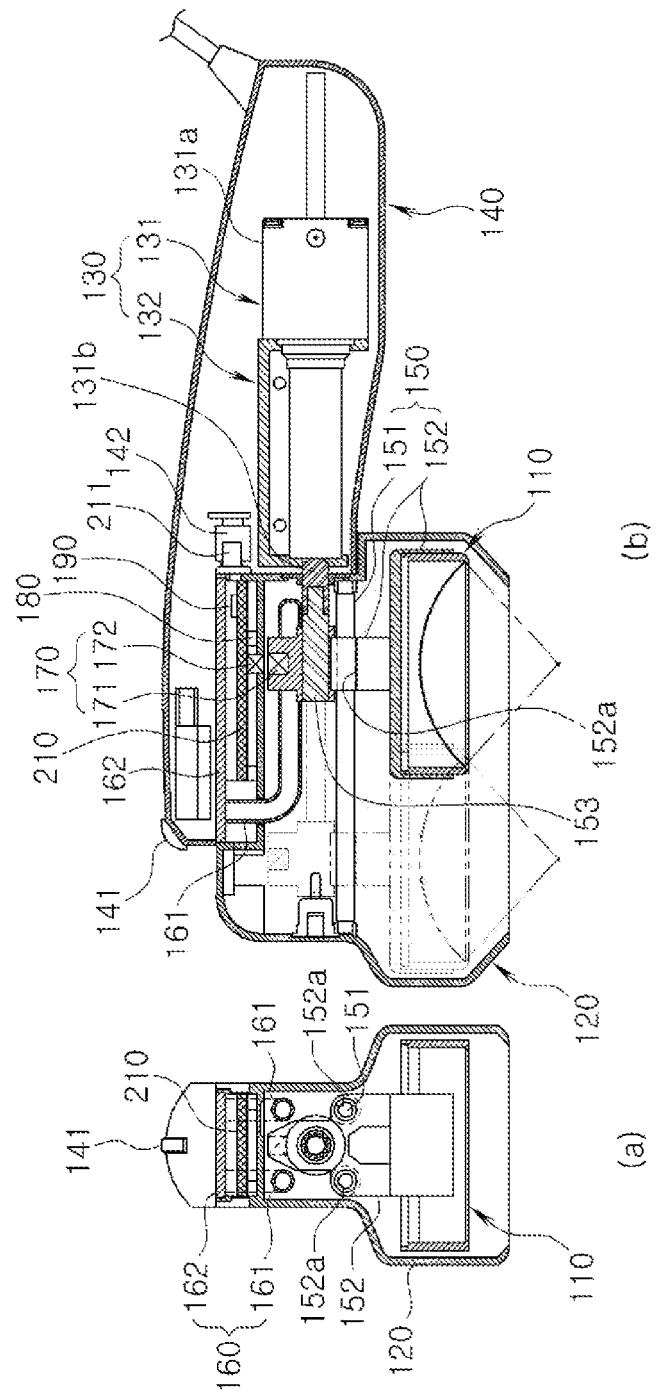

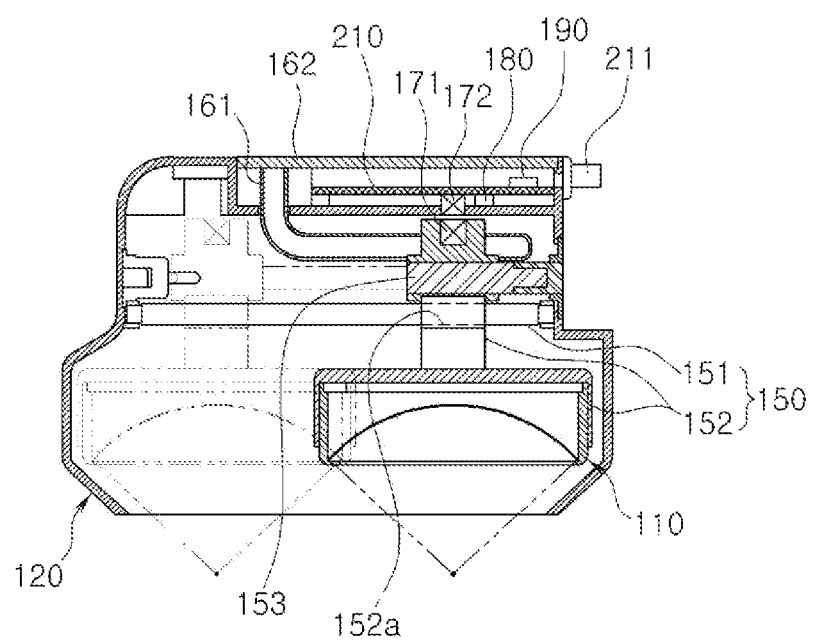
[FIG. 10]

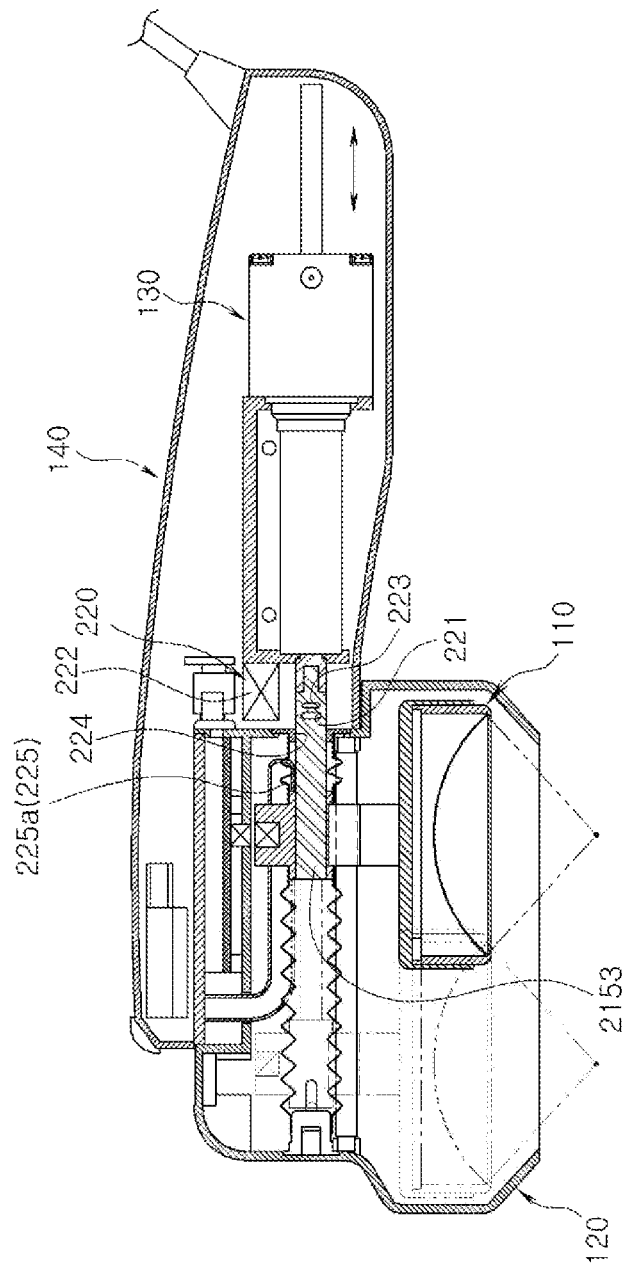
[FIG. 11]

【FIG. 12】
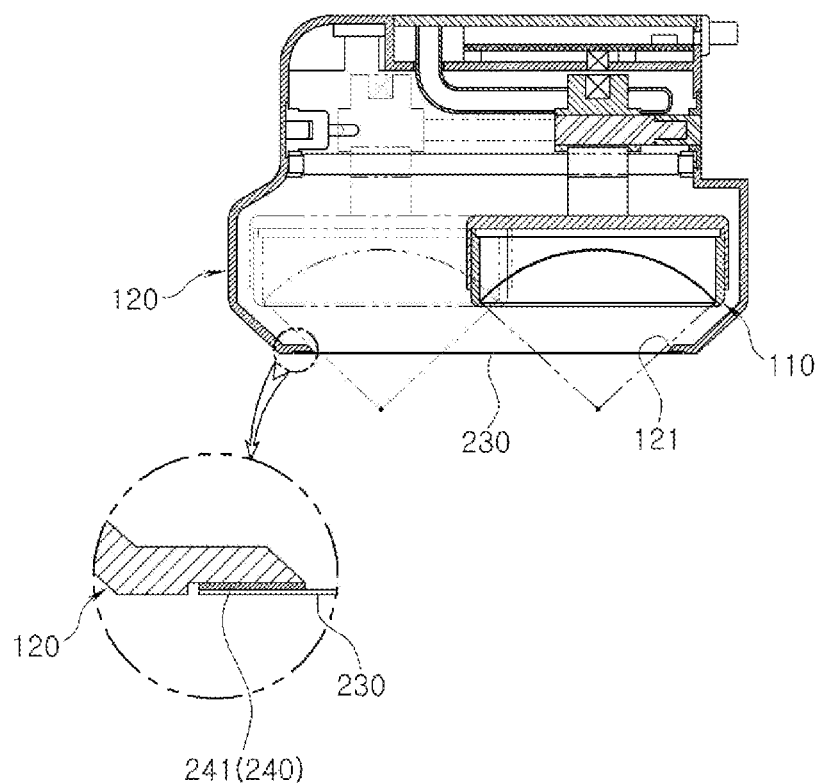
【FIG. 13】
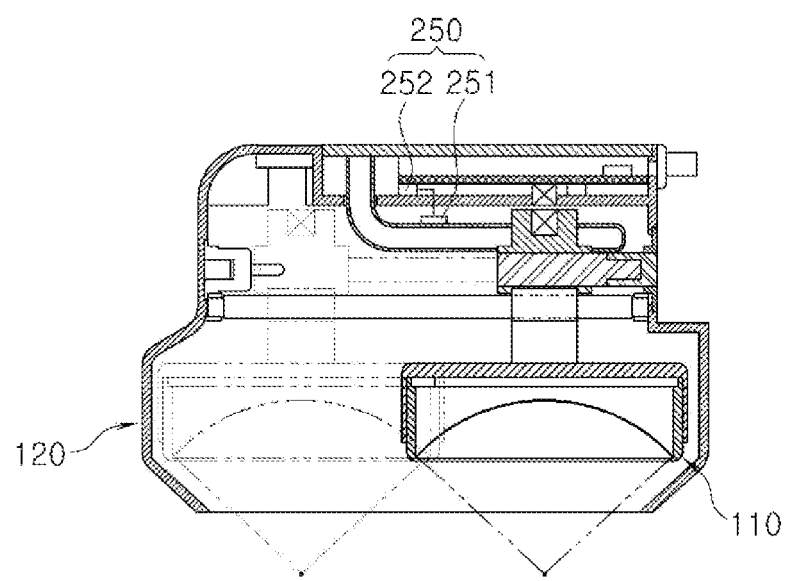

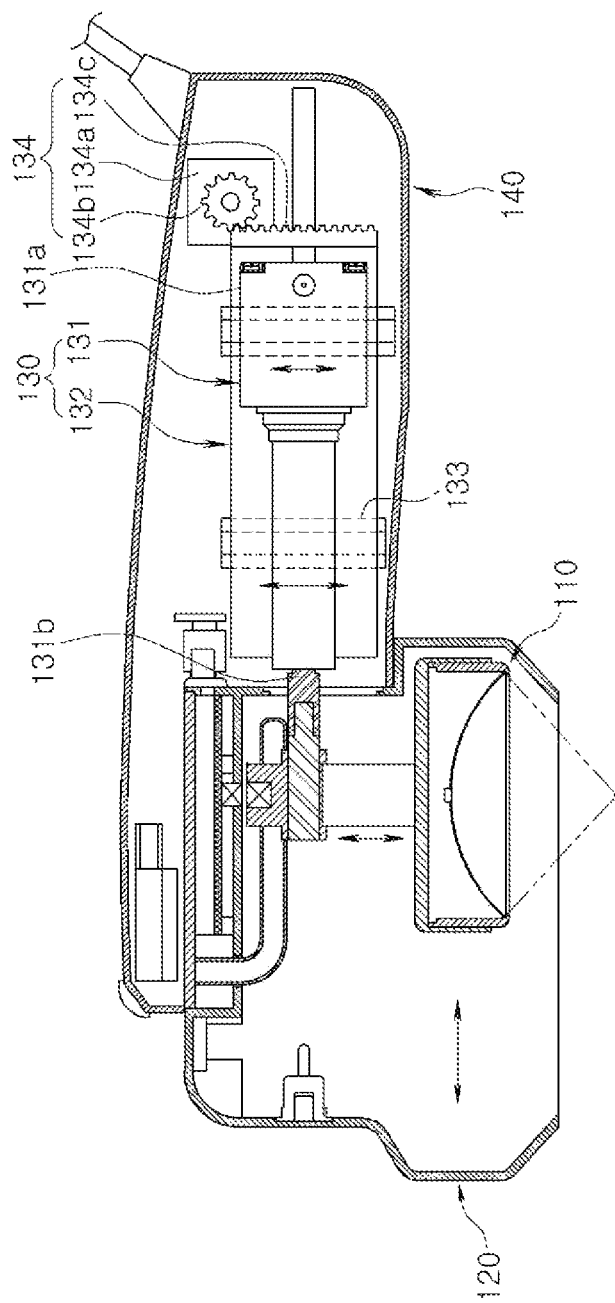
[FIG. 14]

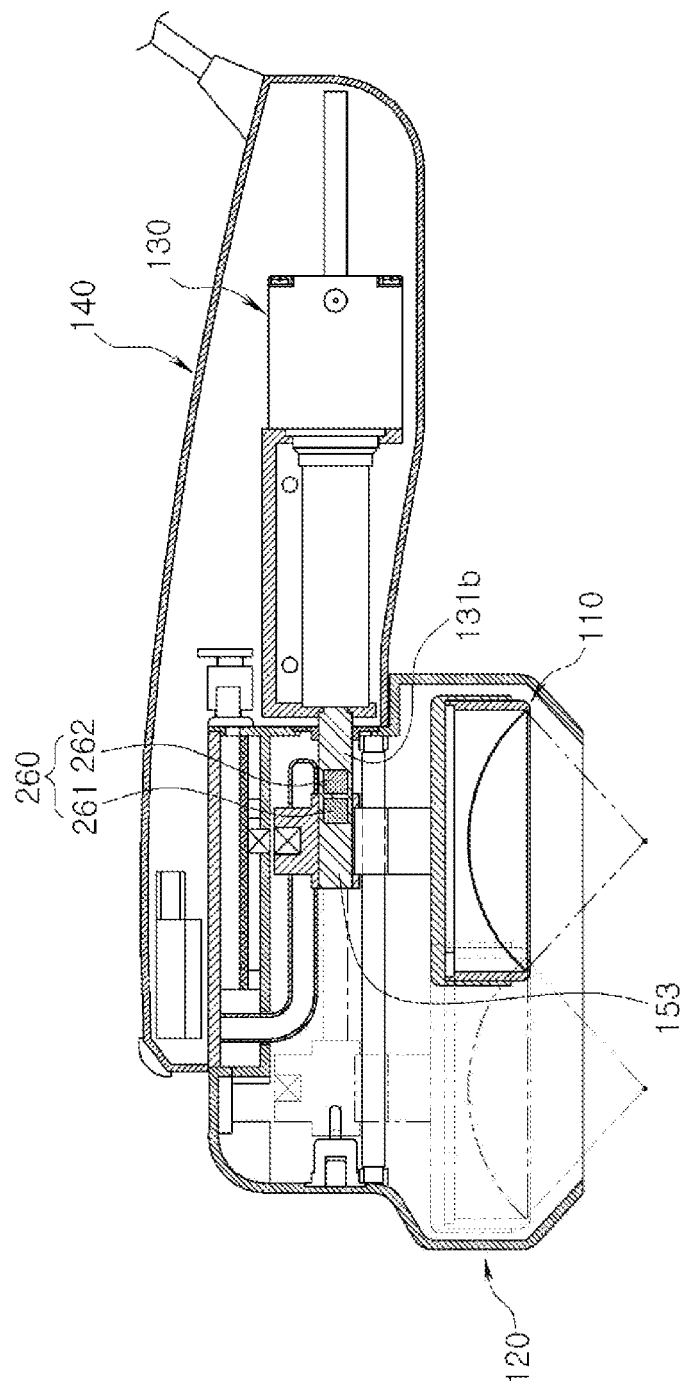
[FIG. 15]

[FIG. 16]
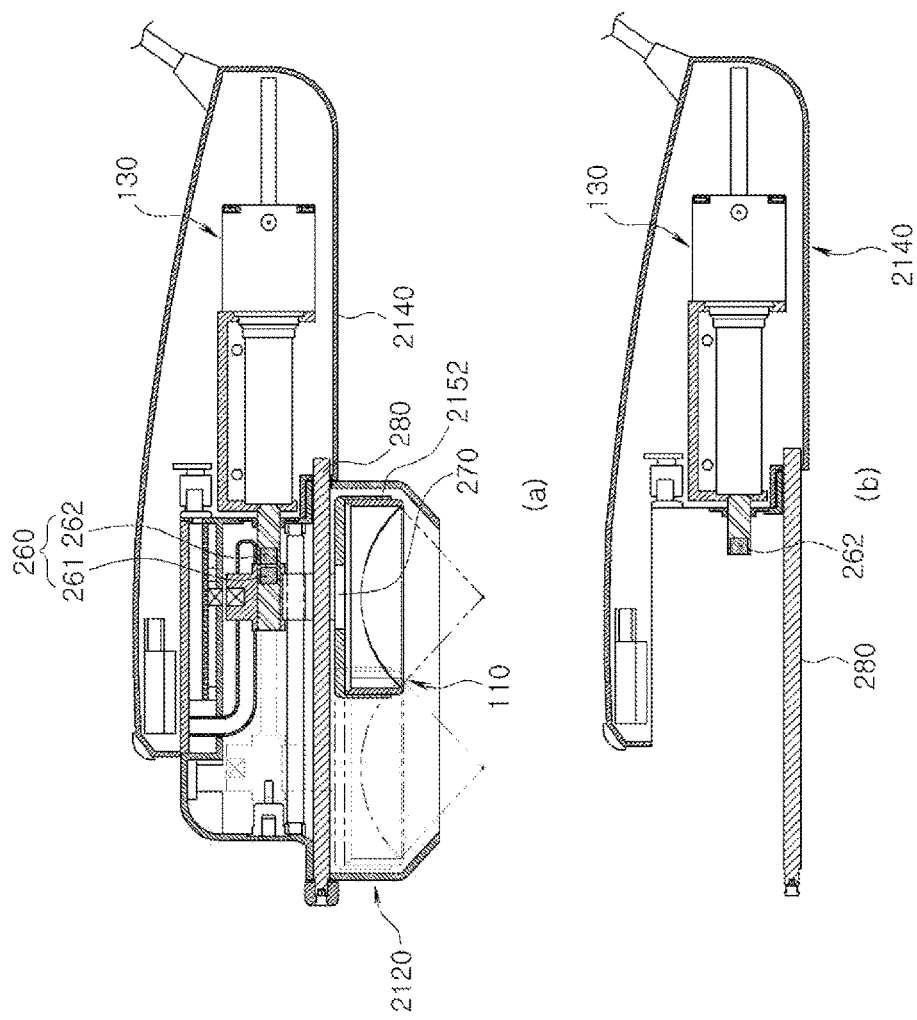

[FIG. 17]
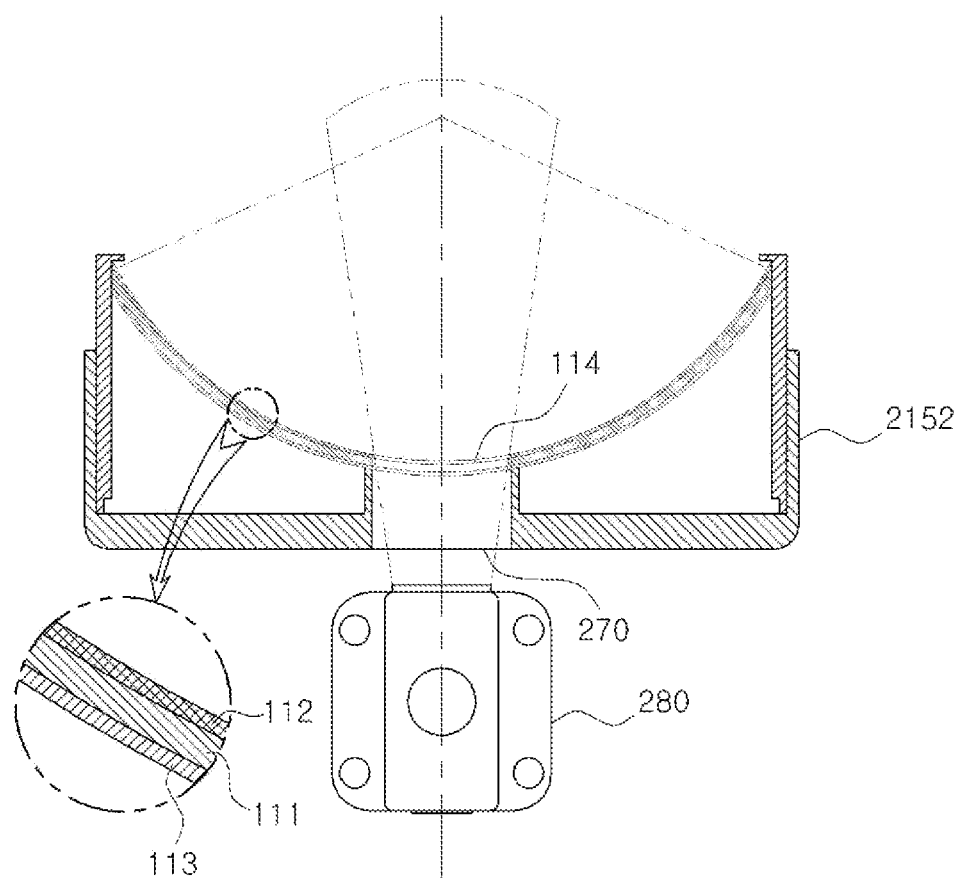

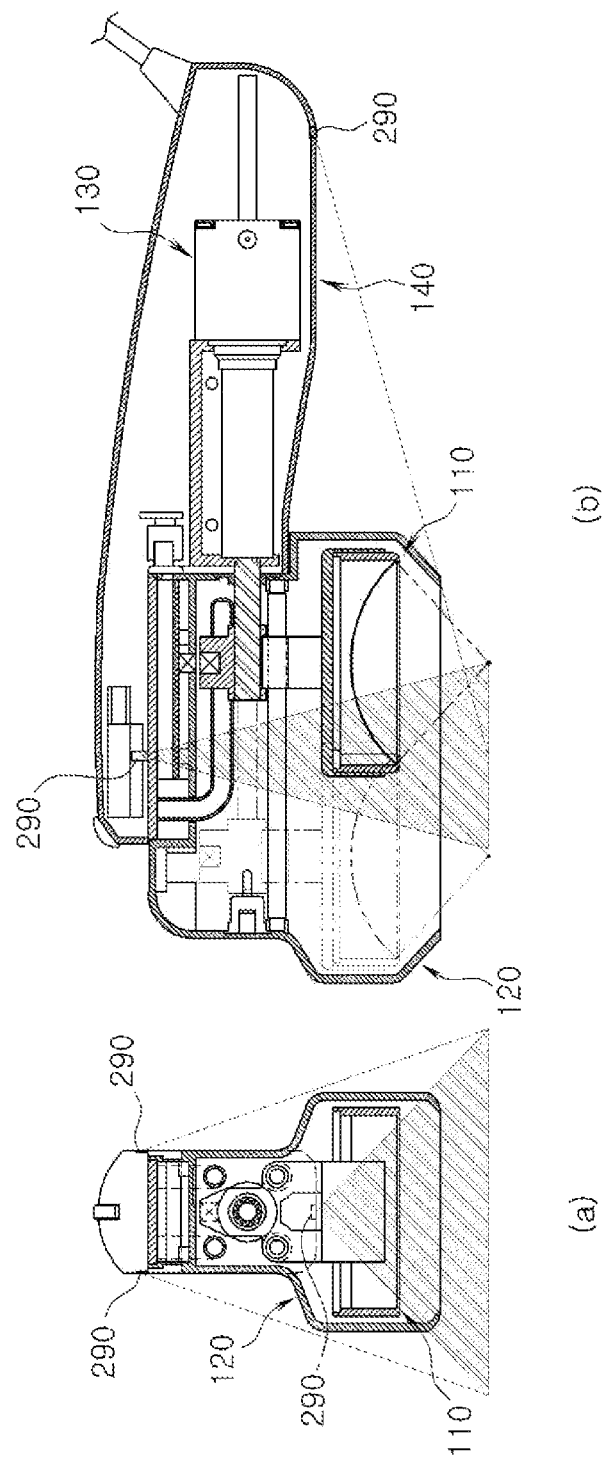
[FIG. 18]

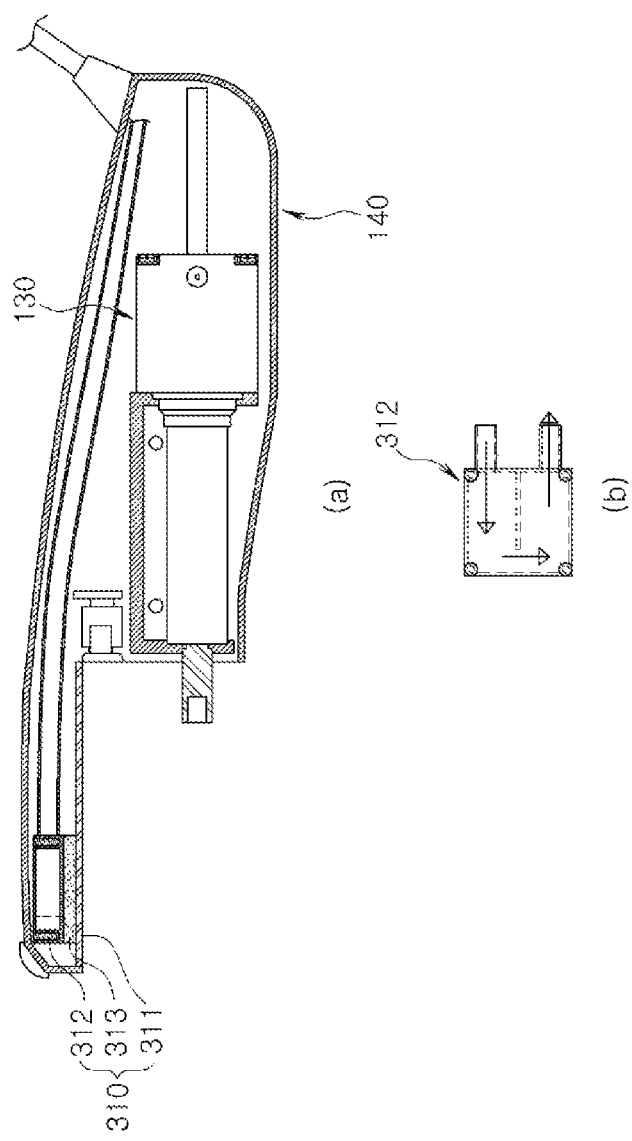
[FIG. 19]

[FIG. 20]
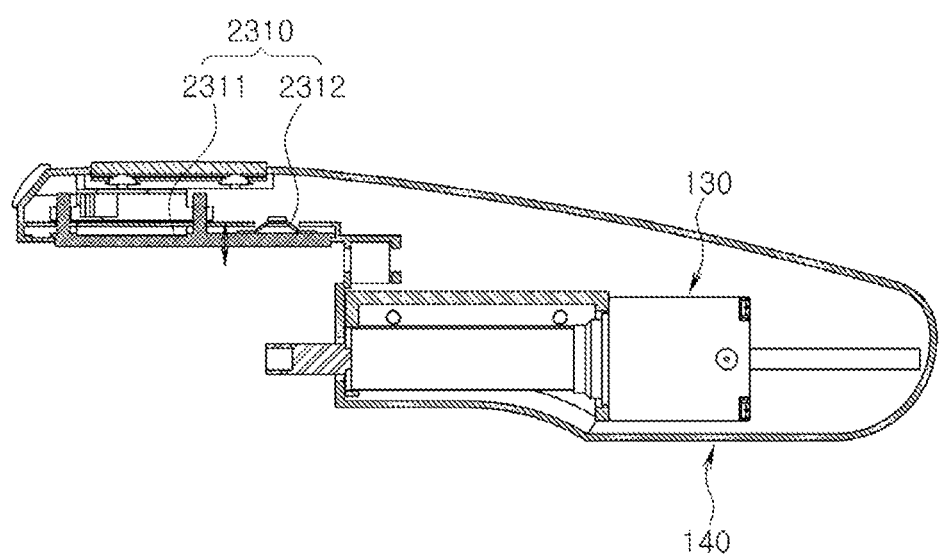
[FIG. 21]
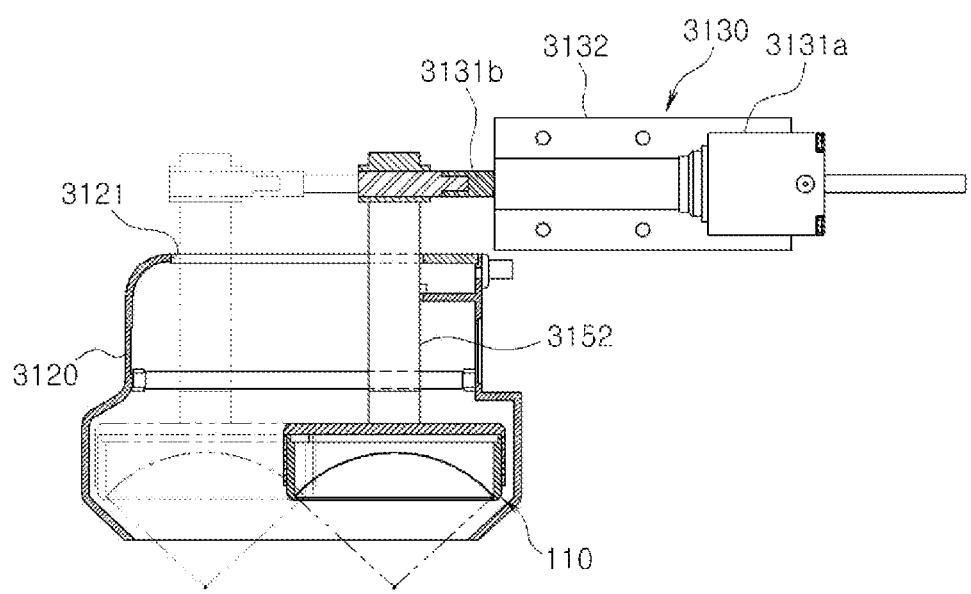

[FIG. 22]
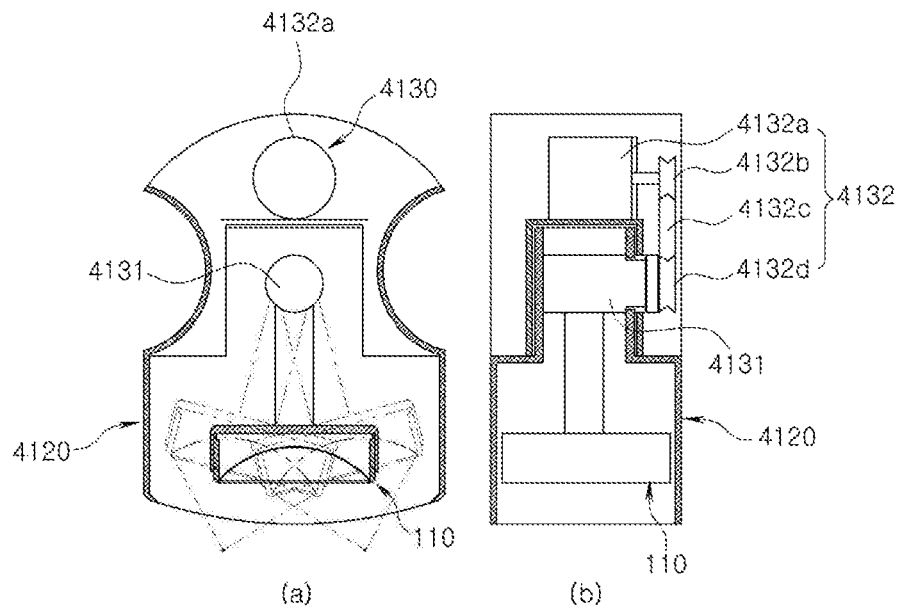
[FIG. 23]
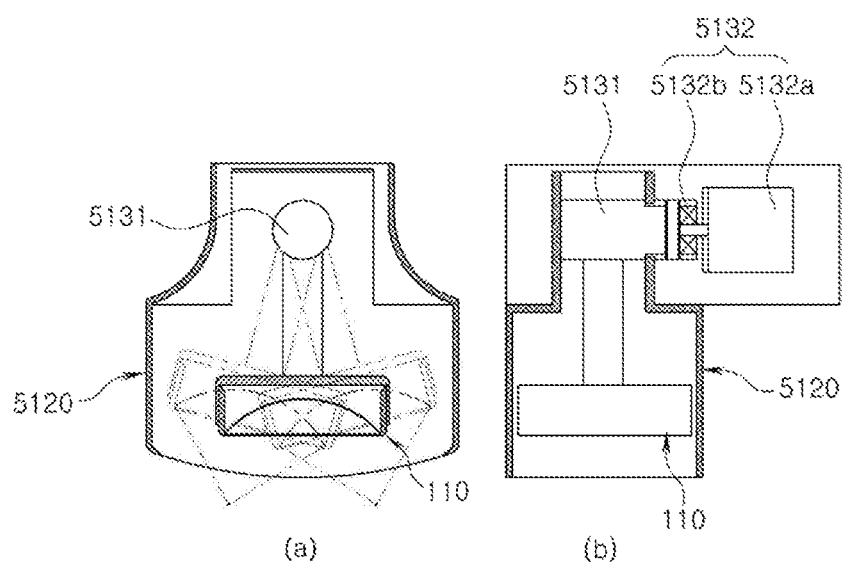

【FIG. 24】
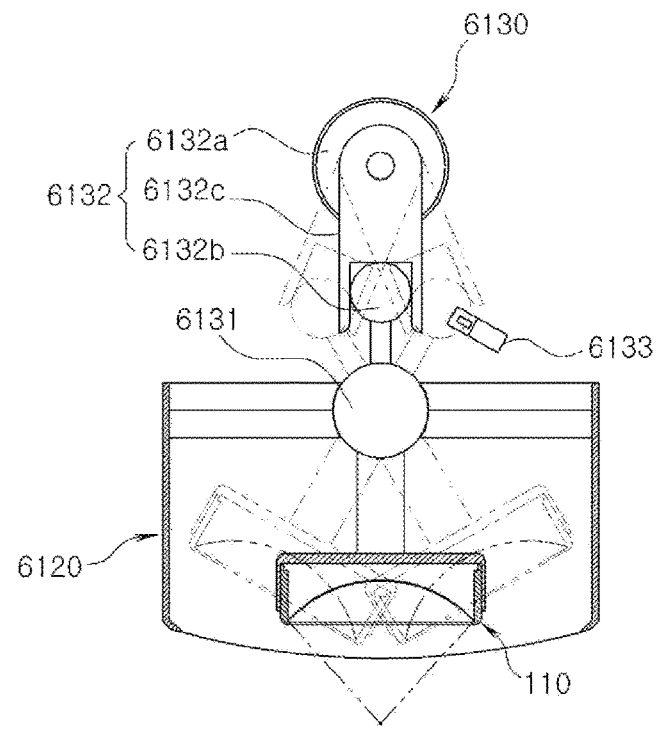
【FIG. 25】
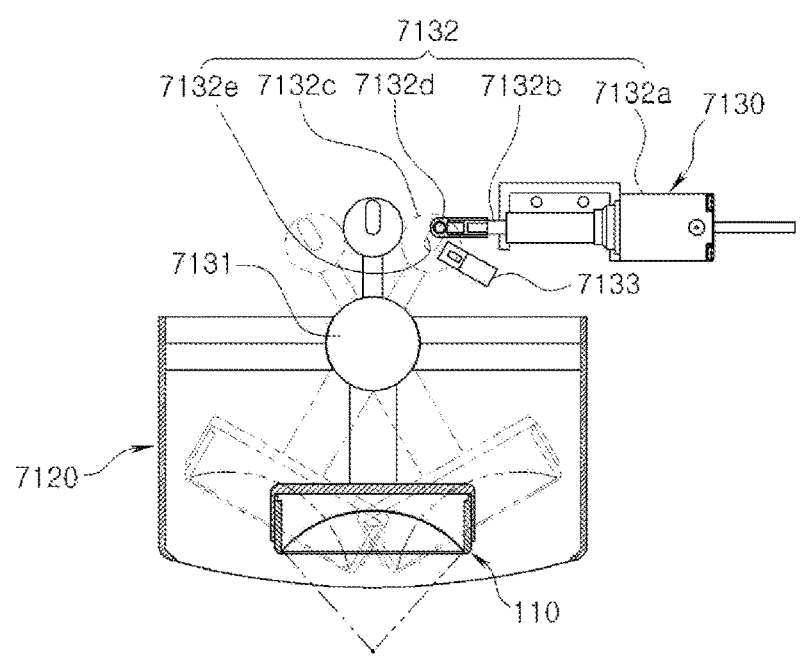

LINE-FOCUSED ULTRASOUND TRANSDUCER AND HIGH-INTENSITY LINE FOCUSED ULTRASOUND GENERATOR INCLUDING SAME

TECHNICAL FIELD

The present invention relates to a line-focused ultrasound transducer which is used in a medical device or the like and a high intensity line-focused ultrasound generation device including same.

BACKGROUND ART

A technology for focusing ultrasound to obtain high intensity focused ultrasound and using this for medical treatment or beauty treatment has been used. Such a treatment is performed by a high intensity focused ultrasound generation device using a focused ultrasound transducer.

In particular, the high intensity focused ultrasound generation device includes a housing and an ultrasound transducer which is fixed within the housing. Further, the ultrasound transducer includes a piezoelectric member of a semi-spherical shape and a first and a second electrode which are respectively formed on both surfaces of the piezoelectric member, and converts electrical signal applied to the first and the second electrodes to ultrasound.

In case of generating ultrasound using a piezoelectric member of a semi-sphere shape, the ultrasound is focused on one point. Such a focused ultrasound is used for treatment of cancer, skin wrinkle care, lipolysis, or the like.

However, the ultrasound which is focused on one point has no problem when it is used for a small area, but when it is used on wide area, it may cause thermal denaturation lesion on a point at one time, long treatment time is required, and it is also problematic that there is no thermal denaturation between the focused points.

Further, in order to regularly or repeatedly treat on wide area using ultrasound focused on one point, the piezoelectric member should be moved, so the mechanical mechanism becomes complicated.

Further, in the conventional high intensity focused ultrasound generation device, since the ultrasound transducer is fixed within the housing, an operator should move the whole device by hand in order to perform treatment for plural treatment areas or wide treatment area.

DETAILED DESCRIPTION OF THE INVENTION

Technical Problem

The present invention has been made in an effort to provide a line-focused ultrasound transducer and a high intensity line-focused ultrasound generation device including the same in which ultrasound is focused in a line so that the treatment time can be reduced and the structure can be simplified.

Further, the present invention has also been made to provide a high intensity line-focused ultrasound in which the line-focused ultrasound transducer can be automatically moved.

Technical Solution

In an embodiment of the present invention, a line-focused ultrasound transducer which focuses in a line shape includes: a therapeutic piezoelectric member having a hollow semi-cylindrical shape; a first electrode portion which is provided on an inner surface of the therapeutic piezoelectric member; and a second electrode portion which is provided on an outer surface of the therapeutic piezoelectric member in correspondence with the first electrode portion.

The line-focused ultrasound transducer may further include an opening portion which is formed at a center of the therapeutic piezoelectric member.

The opening portion may have a plurality of openings which are formed along a longitudinal direction of the therapeutic piezoelectric member with an interval, and piezoelectric members are inserted into the respective openings.

The opening portion may be formed as one opening which is extended along a longitudinal direction of the therapeutic piezoelectric member and a piezoelectric member is inserted into the opening.

The opening may have a rectangular shape or a circular shape.

Each of the first and the second electrode portions may have a plurality of electrodes.

The plurality of electrodes may be electrically insulated from one another and are disposed along a longitudinal direction of the therapeutic piezoelectric member with an interval.

The plurality of electrodes may be electrically insulated from one another and are disposed along a circumferential direction of the therapeutic piezoelectric member with an interval.

According to another embodiment of the present invention, a line-focused ultrasound transducer which focuses in a line shape includes: a plurality of therapeutic piezoelectric members which respectively have a hollow semi-cylindrical shape and are disposed along a longitudinal direction with an interval; a first electrode portion which is provided to respective inner surfaces of the plurality of therapeutic piezoelectric members; and a second electrode portions which is provided to respective inner surfaces of the plurality of therapeutic piezoelectric members.

According to another embodiment of the present invention, a line-focused ultrasound transducer which focuses in a line shape includes: a plurality of therapeutic piezoelectric members which are disposed in a hollow semi-cylindrical shape and are disposed along a circumferential direction with an interval; a first electrode portion which is provided to respective inner surfaces of the plurality of therapeutic piezoelectric members; and a second electrode portions which is provided to respective inner surfaces of the plurality of therapeutic piezoelectric members.

According to another embodiment of the present invention, a high intensity line-focused ultrasound generation device which focuses in a line shape includes: a housing which is filled with an ultrasound transmitting material; a line-focused ultrasound transducer which is provided within the housing to be movable according to one of line-focused ultrasound transducer according to embodiments of the present invention; and a driving unit moving the line-focused ultrasound transducer.

The high intensity line-focused ultrasound generation device may further include a grip which is provided to the housing to be able to be coupled and decoupled.

The driving unit may be disposed within the grip.

The high intensity line-focused ultrasound generation device may further include a linear guiding portion which guides a liner movement of the line-focused ultrasound transducer.

The linear guiding portion may include: a guide rod which is provided on an inner surface of the housing and is extended along a longitudinal direction of the housing; and a support member which supports the line-focused ultrasound transducer such that the line-focused ultrasound transducer slides along the guide rod and has a guide hole to which the guide rod is inserted.

The high intensity line-focused ultrasound generation device may further include a first cooling part which is provided to the housing and cools heat inside the housing.

The first cooling part may include: at least one thermal conductor one end of which is provided within the housing and the other end of which is provided to the outside of the housing; and a heat dissipation plate which is provided to the at least one thermal conductor and dissipates heat transmitted through the conductor to the outside.

The high intensity line-focused ultrasound generation device may further include a first position detecting part which detects a position of the line-focused ultrasound transducer.

The first position detecting part may include: a magnetic body which is provided to the line-focused ultrasound transducer; and a magnetic sensor which is provided to the housing to be correspondent to the magnetic body and detects a position of the magnetic body.

The high intensity line-focused ultrasound generation device may further include: a slider one end of which is connected to the line-focused ultrasound transducer and the other end of which is connected to the driving unit to be able to be coupled and decoupled; and a second position detecting part which detects a position of the line-focused ultrasound transducer.

The second position detecting part may include: a first position hole which is formed at a portion of an end of the slider which is disposed within the grip with reference to an initial state in which the slider is completely pulled by the driving unit; and a proximate sensor which is provided to the grip in correspondence with the first position hole to detect the first position hole.

A second position hole may be further formed at a portion of the other end of the slider which is disposed within the grip such that the slider is detected by the proximate sensor in case that the slider is unintentionally separated from the driving unit.

An opening for inserting and taking out the slider may be formed in the housing and the grip, and a sealing part for preventing the ultrasound transmitting material in the housing from being leaked to the grip through the opening.

The sealing part may have a sealing member of contractible bellows shape which encloses the slider and one end of which is provided to the opening and the other end of which is provided to the line-focused ultrasound transducer.

The high intensity line-focused ultrasound generation device may further include: a first opening part which is formed at a surface of the housing through which the line-focused ultrasound of the line-focused ultrasound transducer passes; a therapeutic window which closes the first opening part and allows the line-focused ultrasound to pass therethrough; and an attaching member which attaches the therapeutic window to the opening part.

The attaching member may be a double-sided adhesive tape.

The high intensity line-focused ultrasound generation device may further include a temperature detecting part which is provide to the housing and detects a temperature inside the housing.

The temperature detecting part may include: a temperature detecting rod which is provided inside the housing; and a temperature sensor which is provided to the outside of the housing and is connected to the temperature detecting rod to detect a temperature of the temperature detecting rod.

The driving unit may include: a first driving part which is provided to the outside of the housing and moves the line-focused ultrasound transducer in a forward/backward direction; and a support bracket which fixes the first driving part at the outside of the housing.

The first driving part may include: a first linear motor which is provide to the outside of the housing; and a moving bar which moves in a forward/backward direction by the first linear motor, the line-focused ultrasound transducer being connected to an end thereof to be able to be coupled and decoupled.

The high intensity line-focused ultrasound generation device may further include a coupling/decoupling unit which is formed to be able to couple and decouple the line-focused ultrasound transducer to and from the driving unit.

The coupling/decoupling unit may include: a first magnet which is provided to the line-focused ultrasound transducer; and a second magnet which is provided to the driving unit in correspondence with first magnet and applies an attractive force to the first magnet.

The high intensity line-focused ultrasound generation device may further include: a second opening part which is formed to the line-focused ultrasound transducer; and an ultrasound transducer for obtaining an image which is provided to the housing or the grip and obtains an image through the second opening part.

The ultrasound transducer for obtaining an image may be provided to the grip and is formed to be separated together when the grip is separated from the housing.

The high intensity line-focused ultrasound generation device may further include a laser oscillator which is provided to the grip and oscillates a laser for position verification on a treatment area.

The high intensity line-focused ultrasound generation device may further include a second cooling part which is provide to a portion of the grip which the housing contacts.

The second cooling part may include: a heat transmitting plate which is provided to the grip and contacts the housing; and a heat exchanger which contacts the heat transmitting plate and exchanges heat of the heat transmitting plate through circulation of cooling water therein.

The high intensity line-focused ultrasound generation device may further include a thermoelectric element which is disposed between the heat transmitting plate and the heat exchanger.

The second cooling part may include: a heat transmitting plate which is provided to the grip to be movable; and an elastic member which is provided between the heat transmitting plate and the grip in a state of adhering to the housing.

The driving unit may include: a rotating shaft to which the line-focused ultrasound transducer is provided and is disposed in a lateral direction in the housing to form a rotation center of the line-focused ultrasound transducer; and a third driving part which is provided to the outside of the housing and applies rotation force to the line-focused ultrasound transducer about the rotating shaft.

The third driving part may include: a second rotation motor which is provided to the outside of the housing; a first pulley which is shaft-coupled to the second rotation motor;

a second pulley which is shaft-coupled to the rotating shaft; and a connecting belt which connects the first and the second pulleys.

The third driving part may include: a third rotation motor which is provided to the outside of the housing and is shaft-coupled to the rotating shaft; and a support bearing which is provided to the housing and rotatably supports a motor shaft of the third rotation motor.

The third driving part may include: a fourth rotation motor which is provided to the outside of the housing; a first pressing protrude which is provide to the rotating shaft; and a power transmitting member one end of which is rotatably connected to an end of the first pressing protrude and the other end of which is shaft-coupled to the fourth rotation motor so as to transmit rotation force of the fourth rotation motor to the rotating shaft together with the first pressing protrude.

The third driving part may include: a second linear motor which is provided to the outside of the housing; a moving bar which moves in a forward/backward direction by the second linear motor; and a second pressing protrude one end of which is provided to the rotating shaft and the other end of which is rotatably connected to the moving bar.

The third driving part may further include: a hinge pin which connects the moving bar to the second pressing protrude to be rotatable; and a hinge hole which is formed at an end of the second pressing protrude and to which the hinge pin is inserted, wherein the hinge hole is formed to be extended in a longitudinal direction of the pressing protrude such that the moving bar moves smoothly in a forward/backward direction while the other end of the second pressing protrude moves in a circumferential direction about the rotating shaft.

Advantages Effects

According to the present invention, since ultrasound is focused in a line due to the therapeutic piezoelectric member having the hollow semi-cylindrical shape, time for treatment can be reduced and treatment effect can be maximized, compared to the device in which ultrasound is focused on one point.

In addition, according to the embodiments of the present invention, since the ultrasound transducer automatically moves in a housing by a driving unit, the focusing point of the ultrasound transducer can automatically move on a plurality of target sheets or on a long target sheet (e.g., treatment area), without a user's effort to move the housing.

BRIEF DESCRIPTIONS OF DRAWINGS

FIG. 1 is a perspective view of a line-focused ultrasound transducer according to a first embodiment of the present invention.

FIG. 2 is a sectional view of a line-focused ultrasound transducer of FIG. 1.

FIG. 3 schematically shows a line-focused ultrasound transducer according to a second embodiment of the present invention, where (a) is a top view and (b) is a sectional view.

FIG. 4 schematically shows a line-focused ultrasound transducer according to a third embodiment of the present invention, where (a) is a top view and (b) is a sectional view.

FIG. 5 schematically shows a line-focused ultrasound transducer according to a fourth embodiment of the present invention, where (a) is a top view, (b) is a sectional view and (c) is a sectional view taken along a line V-V of (b).

FIG. 6 schematically shows a line-focused ultrasound transducer according to a fifth embodiment of the present invention, where (a) is a top view and (b) is a sectional view.

FIG. 7 schematically shows a line-focused ultrasound transducer according to a sixth embodiment of the present invention, where (a) is a top view, (b) is a sectional view and (c) is a sectional view taken along a line VII-VII of (b).

FIG. 8 schematically shows a line-focused ultrasound transducer according to a seventh embodiment of the present invention, where (a) is a top view and (b) is a sectional view.

FIG. 9 schematically shows a high intensity line-focused ultrasound generation device according to a first embodiment of the present invention, where (a) is a sectional view seen from the front and (b) is a sectional view seen from the side.

FIG. 10 is a sectional view showing a housing and parts therein of a high intensity line-focused ultrasound generation device of FIG. 9.

FIG. 11 is a sectional view schematically showing a high intensity line-focused ultrasound generation device according to a second embodiment of the present invention.

FIG. 12 is a sectional view schematically showing a high intensity line-focused ultrasound generation device according to a third embodiment of the present invention.

FIG. 13 is a sectional view schematically showing a high intensity line-focused ultrasound generation device according to a fourth embodiment of the present invention.

FIG. 14 is a sectional view schematically showing a high intensity line-focused ultrasound generation device according to a fifth embodiment of the present invention.

FIG. 15 is a sectional view schematically showing a high intensity line-focused ultrasound generation device according to a sixth embodiment of the present invention.

FIG. 16 is a sectional view schematically showing a high intensity line-focused ultrasound generation device according to a seventh embodiment of the present invention, wherein (a) is a sectional view and (b) is a sectional view of a grip which is separated from the housing.

FIG. 17 schematically shows a line-focused ultrasound transducer of a high intensity line-focused ultrasound generation device of FIG. 16.

FIG. 18 schematically shows a high intensity line-focused ultrasound generation device according to an eighth embodiment of the present invention, where (a) is a sectional view seen from the front and (b) is a sectional view seen from the side.

FIG. 19 schematically shows a grip of a high intensity line-focused ultrasound generation device according to a ninth embodiment of the present invention, where (a) is a sectional view and (b) is a conceptual diagram of a heat exchanger which is provided to the grip.

FIG. 20 is a sectional view schematically showing a grip of a high intensity line-focused ultrasound device according to a tenth embodiment of the present invention.

FIG. 21 is a sectional view schematically showing a high intensity line-focused ultrasound generation device according to an eleventh embodiment of the present invention.

FIG. 22 schematically shows a high intensity line-focused ultrasound generation device according to a twelfth embodiment of the present invention, where (a) is a sectional view seen from the side and (b) is a sectional view seen from the front.

FIG. 23 schematically shows a high intensity line-focused ultrasound generation device according to a thirteenth embodiment of the present invention, where (a) is a sectional view seen from the side and (b) is a sectional view seen from the front.

FIG. 24 is a sectional view schematically showing a high intensity line-focused ultrasound generation device according to a fourteenth embodiment of the present invention.

FIG. 25 is a sectional view schematically showing a high intensity line-focused ultrasound generation device according to a fifteenth embodiment of the present invention.

DETAILED DESCRIPTION OF THE EMBODIMENTS

Hereinafter, embodiments of the present invention will be described in detail with reference to the accompanying drawings. However, the present invention can be realized as various ways and is not limited to the embodiments which will be described.

FIG. 1 is a perspective view of a line-focused ultrasound transducer according to a first embodiment of the present invention, and FIG. 2 is a sectional view of a line-focused ultrasound transducer of FIG. 1.

A line-focused ultrasound transducer 110 according to a first embodiment of the present invention focuses ultrasound in a line, and as shown in FIG. 1 and FIG. 2 may be installed within a housing 120 of a high intensity line-focused ultrasound generation device via a supporting member 152.

Here, the housing 120 may have a first opening part (121 in FIG. 12) at a frontal end thereof, and a therapeutic window (230 in FIG. 12) may be provided to the first opening part (121 in FIG. 12). Accordingly, the ultrasound generated in the ultrasound transducer 110 is focused in a line shape on a therapeutic portion via the treatment window 230 through the first opening part 121. Further, an inside space of the housing 120 may be filled with ultrasound transmitting material (not shown).

In addition, not shown in the drawings, the line-focused ultrasound transducer 110 according to the first embodiment of the present invention may be electrically connected to a pulse power generator (not shown) via a cable (not shown).

The line-focused ultrasound transducer 110 according to the first embodiment of the present invention, as shown in FIG. 1 and FIG. 2, includes a therapeutic piezoelectric member 111, a first electrode portion 112 and a second electrode portion 113. The line-focused ultrasound transducer 110 is also called as a vibrator.

The therapeutic piezoelectric member 111, as shown in FIG. 1, has a hollow semi-cylindrical shape. The therapeutic piezoelectric member 111 may be formed of various materials such as ceramic, complex piezoelectric material, single crystal quartz or the like which can converts electrical signal to mechanical vibration. Further, vibration frequency of the therapeutic piezoelectric member 111 is determined depending on the thickness thereof, and in the embodiment of the present invention the range of the vibration frequency is not limited and all vibration frequency which can be used as the therapeutic piezoelectric member 111 can be used. That is, all range of vibration frequency which can be used for ultrasound treatment can be included.

Further, the size of the therapeutic piezoelectric member 111 is not limited such that it can be suitably realized in accordance with the magnitude of energy of the high intensity line-focused generation device and use of treatment.

The first electrode portion 112 and the second electrode portion 113 are formed to contact respectively an inner surface (which is an inner surface of a hollow semi-cylindrical shape and is a surface facing a focus) and an outer surface (which is an outer surface of a hollow semi-cylindrical shape and is a surface opposite to a surface facing a focus) and to correspond to one another. For example, the first and the second electrode portions 112 and 113 are formed of metal such as silver which has a good electrical conductivity.

The first and the second electrode portions 112 and 113 may be electrically connected to a pulse power generator (not shown) so that the pulse current generated by the pulse power generator (not shown) can be applied thereto. That is, the first electrode 112 may be electrically connected to one of a positive electrode and a negative electrode (or a ground electrode) of the pulse power generator (not shown) via a first electrically conductive line (not shown), and the second electrode 113 may be electrically connected to the other of a positive electrode and a negative electrode (or a ground electrode) of the pulse power generator (not shown) via a second electrically conductive line (not shown). Accordingly, the pulse current generated by the pulse power generator (not shown) is applied to the first and the second electrode portions 112 and 113, so the applied pulse current flows through the therapeutic piezoelectric member 111. If the pulse current flows through the therapeutic piezoelectric member 111, the therapeutic piezoelectric member 111 vibrates due to the piezoelectric effect.

The therapeutic piezoelectric member 111 vibrates if the pulse current is applied to the first and the second electrode portions 112 and 113 so that the pulse current flows through the therapeutic piezoelectric member 111, and this vibration has ultrasound characteristics and ultrasound is generated in the ultrasound transmitting material (not shown) surrounding the therapeutic piezoelectric member 111 and this ultrasound transmits via the ultrasound transmitting material (not shown) and is focused at the treatment area in the shape of a line.

Hereinafter, referring to FIG. 3, the line-focused ultrasound transducer according to a second embodiment of the present invention will be described.

FIG. 3 schematically shows a line-focused ultrasound transducer according to a second embodiment of the present invention, where (a) is a top view and (b) is a sectional view.

The line-focused ultrasound transducer 2110 according to a second embodiment of the present invention, as shown in FIG. 3, is equal to the first embodiment of the present invention except the point of further including an opening portion 2114 and an image obtaining piezoelectric member 2115, so explanation only for the opening portion 2114 and the image obtaining piezoelectric member 2115 will be made.

The opening portion 2114 may be formed at a center of a therapeutic piezoelectric member 2111. In more detail, the opening portion 2114 may be formed as a plurality of openings 2114a to 2114e which are formed along a length direction of the therapeutic piezoelectric member 2111 with an interval.

The image obtaining piezoelectric member 2115 may be fitted into the respective openings 2114a to 2114e.

Accordingly, treatment for the treatment area may be performed using the therapeutic piezoelectric member 2111 and at the same time the image of the treatment area can be obtained using the image obtaining piezoelectric member 2115.

At this time, the therapeutic piezoelectric member 2111 and the first and the second electrode portions 2112 and 2113 are different from that of the first embodiment by the opening portion 2114, so new reference numerals were used, but since the function and the role are equal to those of the first embodiment, detailed descriptions will be omitted.

Hereinafter, referring to FIG. 4, a line-focused ultrasound transducer according to a third embodiment of the present invention will be described.

FIG. 4 schematically shows a line-focused ultrasound transducer according to a third embodiment of the present invention, where (a) is a top view and (b) is a sectional view.

The line-focused ultrasound transducer 3110 according to a third embodiment of the present invention, as shown in FIG. 4, is equal to the first embodiment of the present invention except the point of further including an opening portion 3114 and an image obtaining piezoelectric member 3115, so explanation only for the opening portion 3114 and the image obtaining piezoelectric member 3115 will be made.

The opening portion 3114 may be formed at a center of a therapeutic piezoelectric member 3111. In particular, the opening portion 3114 may be formed as one opening 3114a. For example, the opening 3114a may have a rectangular shape as shown in FIG. 4, but it may also a circular shape.

The image obtaining piezoelectric member 3115 may be fitted into the opening 3114a.

Accordingly, treatment for the treatment area may be performed using the therapeutic piezoelectric member 3111 and at the same time the image of the treatment area can be obtained using the image obtaining piezoelectric member 3115. In particular, since one opening 3114a is formed to be ling, images for an area wider than that of the second embodiment of the present invention.

At this time, the therapeutic piezoelectric member 3111 and the first and the second electrodes 3112 and 3113 are different from that of the first embodiment by the opening portion 3114, so new reference numerals were used, but since the function and the role are equal to those of the first embodiment, detailed descriptions will be omitted.

Hereinafter, referring to FIG. 5, a line-focused ultrasound transducer according to a fourth embodiment of the present invention will be described.

FIG. 5 schematically shows a line-focused ultrasound transducer according to a fourth embodiment of the present invention, where (a) is a top view, (b) is a sectional view and (c) is a sectional view taken along a line V-V of (b).

The line-focused ultrasound transducer 4110 according to a fourth embodiment of the present invention, as shown in FIG. 5, is equal to the first embodiment of the present invention except a first electrode portion 4112 and a second electrode portion 4113, so explanation only for the first electrode portion 4112 and the second electrode portion 4113 will be made. In addition, the same reference numeral for the same elements with the first embodiment of the present invention will be used.

The first electrode portion 4112 may be composed of a plurality of first electrodes 4112a to 4112e, and the second electrode portion 4113 may be composed of a plurality of second electrodes 4112a to 4112e corresponding to the plurality of first electrodes 4113a to 4113e. In more detail, the plurality of the first electrodes 4112a to 4112e and the plurality of the second electrodes 4113a to 4113e may be electrically insulated from one another and may be disposed along a longitudinal direction of the therapeutic piezoelectric member 111 with an interval therebetween.

Furthermore, the first electrodes 4112a to 4112e and the second electrodes 4113a to 4113e may be electrically connected to a pulse power generator (not shown) via a focusing controller (not shown) so that the pulse current generated by the pulse power generator can be applied thereto. Accordingly, the pulse current generated by the pulse power generator is applied to the electrode among the first electrodes 4112a to 4112e and the second electrodes 4113a to 4113e which are selected by the focusing controller, and the applied current flows through the therapeutic piezoelectric member 111. If the pulse current flows through the therapeutic piezoelectric member 111, the therapeutic piezoelectric member 111 vibrates due to the piezoelectric effect.

The focusing controller (not shown) turns on or off the current applied to at least one of the first electrodes 4112a to 4112e and the second electrodes 4113a to 4113e so as to regulate the intensity of ultrasound generated respective positions of the therapeutic piezoelectric member 111.

Accordingly, by selectively operating a portion of the first electrodes 4112a to 4112e and the second electrodes 4113a to 4113e by the control of the focusing controller (not shown), the ultrasound focusing area can be regulated.

Hereinafter, referring to FIG. 6, a line-focused ultrasound transducer according to a fifth embodiment of the present invention will be described.

FIG. 6 schematically shows a line-focused ultrasound transducer according to a fifth embodiment of the present invention, where (a) is a top view and (b) is a sectional view.

The line-focused ultrasound transducer 5110 according to a fifth embodiment of the present invention, as shown in FIG. 6, is equal to the first embodiment of the present invention except a first electrode portion 5112 and a second electrode portion 5113, so explanation only for the first electrode portion 5112 and the second electrode portion 5113 will be made. In addition, the same reference numeral for the same elements with the first embodiment of the present invention will be used.

The first electrode portion 5112 may be composed of a plurality of first electrodes 5112a to 5112h, and the second electrode portion 5113 may be composed of a plurality of second electrodes 5112a to 5112h corresponding to the plurality of first electrodes 5113a to 5113h. In more detail, the plurality of the first electrodes 5112a to 5112h and the plurality of the second electrodes 5113a to 5113h may be electrically insulated from one another and may be disposed along a circumferential direction of the therapeutic piezoelectric member 111 with an interval therebetween.

Furthermore, the first electrodes 5112a to 5112h and the second electrodes 5113a to 5113h may be electrically connected to a pulse power generator (not shown) via a focusing controller (not shown) so that the pulse current generated by the pulse power generator can be applied thereto. Accordingly, the pulse current generated by the pulse power generator is applied to the electrode among the first electrodes 5112a to 5112h and the second electrodes 5113a to 5113h which are selected by the focusing controller, and the applied current flows through the therapeutic piezoelectric member 111. If the pulse current flows through the therapeutic piezoelectric member 111, the therapeutic piezoelectric member 111 vibrates due to the piezoelectric effect.

The focusing controller (not shown) turns on or off the current applied to at least one of the first electrodes 5112a to 5112h and the second electrodes 5113a to 5113h so as to regulate the intensity of ultrasound generated respective positions of the therapeutic piezoelectric member 111.

Accordingly, according to the control of the focusing controller (not shown) a mechanical vibration does almost not occur at a line of a longitudinal direction of a center of the therapeutic piezoelectric member 111, so ultrasound can be focused shortly in a longitudinal direction. Further, by selectively operating a portion of the first electrodes 5112a to 5112h and the second electrodes 5113a to 5113h by the control of the focusing controller (not shown), the ultrasound focusing area can be regulated.

Hereinafter, referring to FIG. 7, a line-focused ultrasound transducer according to a sixth embodiment of the present invention will be described.

FIG. 7 schematically shows a line-focused ultrasound transducer according to a sixth embodiment of the present invention, where (a) is a top view, (b) is a sectional view and (c) is a sectional view taken along a line VII-VII of (b).

The line-focused ultrasound transducer 6110 according to a sixth embodiment of the present invention, as shown in FIG. 7, is equal to the first embodiment of the present invention except a therapeutic piezoelectric member 6110 and a first electrode portion 6112 and a second electrode portion 6113, so explanation only for the therapeutic piezoelectric member 6110 and the first electrode portion 5112 and the second electrode portion 5113 will be made.

The therapeutic piezoelectric members 6111a to 6111e have a hollow semi-cylindrical shape respectively and may be disposed in a longitudinal direction with an interval.

The first electrode portion 6112 may be provided to the respective inner surfaces of the therapeutic piezoelectric members 6111a to 6111e, and the second electrode portions 6113 may be provided to the respective outer surfaces of the therapeutic piezoelectric members 6111a to 6111e.

Accordingly, the therapeutic piezoelectric members 6111a to 6111e may be used respectively or simultaneously.

At this time, the main functions and the main roles of the therapeutic piezoelectric member 6111 and the first electrode portion 6112 and the second electrode portion 6113 are equal to those of the first embodiment, so detailed description thereof will be omitted.

Hereinafter, referring to FIG. 8, a line-focused ultrasound transducer according to a seventh embodiment of the present invention will be described.

FIG. 8 schematically shows a line-focused ultrasound transducer according to a seventh embodiment of the present invention, where (a) is a top view and (b) is a sectional view.

The line-focused ultrasound transducer 7110 according to a seventh embodiment of the present invention, as shown in FIG. 8, is equal to the first embodiment of the present invention except a therapeutic piezoelectric member 7111 and a first electrode portion 7112 and a second electrode portion 7113, so explanation only for the therapeutic piezoelectric member 7111 and the first electrode portion 7112 and the second electrode portion 7113 will be made.

The plurality of the therapeutic piezoelectric members 7111a to 7111h may be disposed along circumferential direction while being disposed in a hollow semi-cylindrical shape.

The first electrode 7112 may be provided at the respective inner surface of the plurality of the therapeutic piezoelectric members 7111a to 7111h, and the second electrode 7113 may be provided at the respective outer surface of the plurality of the therapeutic piezoelectric members 7111a to 7111h in correspondence to the first electrode 7112.

Accordingly, the plurality of the therapeutic piezoelectric members 7111a to 7111h may be used independently or together as the sixth embodiment.

At this time, the main function and role of the therapeutic piezoelectric member 7111 and the first and the second electrode portions 7112 and 7113 is equal to those of the first embodiment, so detail explanation for the same will be omitted.

Meanwhile, the line-focused ultrasound transducers 110, 2110, 3110, 4110, 6110 and 7110 may be installed to the high intensity line-focused ultrasound generation device. Hereinafter, the high intensity line-focused ultrasound generation device including the line-focused ultrasound transducer will be described referring to FIG. 9 to FIG. 25.

Hereinafter, referring to FIG. 9 and FIG. 10, a high intensity line-focused ultrasound generation device according to a first embodiment of the present invention will be described.

FIG. 9 schematically shows a high intensity line-focused ultrasound generation device according to a first embodiment of the present invention, where (a) is a sectional view seen from the front and (b) is a sectional view seen from the side.

FIG. 10 is a sectional view showing a housing and parts therein of a high intensity line-focused ultrasound generation device of FIG. 9.

The high intensity line-focused ultrasound generation device according to a first embodiment of the present invention generates an ultrasound which is focused in a line shape, and as shown in FIG. 9 and FIG. 10, includes a housing 120, a line-focused ultrasound transducer 110 and a driving unit 130

The housing 120 is filled with ultrasound transmitting material (not shown) and may have a sealed structure in order to prevent the ultrasound transmitting material from being leaked.

In addition, the housing 120 has a first opening part (121 in FIG. 12) at a frontal end thereof, and a therapeutic window (230 in FIG. 12) may be mounted at the first opening part 121. Accordingly, the ultrasound generated by the line-focused ultrasound transducer 110 is focused in a line shape on a therapeutic portion via the therapeutic window 230 through the first opening part 121.

The line-focused ultrasound transducer 110 is movably disposed within the housing 120 and may be the line-focused ultrasound transducer of the embodiments described in the above, so detailed description will be omitted.

The driving unit 130 plays a role of moving the line-focused ultrasound transducer 110. Hereinafter, referring to (b) of FIG. 9, the driving unit 130 will be explained in detail.

The driving unit 130 may include a first driving part 131 which is disposed at the outside of the housing 120 and moves the line-focused ultrasound transducer 110 in a forward/backward direction and a support bracket 132 which fixes the first driving part 131 to the outside of the housing 120.

For example, the first driving part 131 may include a first linear motor 131a which is provided at the outside of the housing 120 and a moving bar 131b which moves in a forward/backward direction by the first linear motor 131a and at an end of which the line-focused ultrasound transducer 110 is connected to be selectively coupled.

Accordingly, while the moving bar 131b moves in a forward/backward direction by the driving operation of the first linear motor 131a which is fixed to the fixing bracket 132, the line-focused ultrasound transducer 110 which is connected thereto also moves in a forward/backward direction. During this movement, the line-focused ultrasound transducer 110 performs the treatment.

Further, the high intensity line-focused ultrasound generation device according to a first embodiment of the present invention, as shown in (b) of FIG. 9, may further include a grip 140 which is separably connected to the housing 120. In this case, the driving unit 130 may be provided within the grip 140. That is, the first linear motor 131a may be disposed within the grip 140 by a support bracket 132 which is fixed in the grip 140.

Accordingly, since the linear motor 131a is not exposed to the outside, the outer appearance of the whole device can be improved, and since the first linear motor 131a which is generally long is disposed within the long grip 140, the space of the grip 140 can be effectively used.

Further, the high intensity line-focused ultrasound generation device according to a first embodiment of the present invention, as shown in (b) of FIG. 9 and FIG. 10, may further include a linear guiding part 150 which guides a linear movement of the line-focused ultrasound transducer 110.

For example, the linear guiding part 150 may include a guiding rod which is elongated a longitudinal axis of the hosing 120 in an inner surface of the housing 120 and a support member 152 which supports the line-focused ultrasound transducer 110 such that the line-focused ultrasound transducer slides along the guiding rod, and a guiding hole 152a into which the guiding rod 151 is inserted may be formed in the support member 152. Further, the linear guiding part 150 may further include a slider 153 one end of which is provided to the support member 152 of the line-focused ultrasound transducer 110 and the other end of which is separably connected to the driving unit 130.

Accordingly, since the line-focused ultrasound transducer 110 can maintain a linear movement state without shaking horizontally and vertically due to the linear guiding part 150 while moving by the driving unit 130, the precise control of the high intensity focused ultrasound generation device is possible.

In addition, the high intensity line-focused ultrasound generation device according to a first embodiment of the present invention, as shown in FIG. 9 and FIG. 10, may further include a first cooling part 160 which is provided to the housing 120 and cools the inside of the housing 120.

For example, the first cooling part 160 may include at least one thermal conductor 161 one end of which is disposed within the housing 120 and the other end of which is disposed in the outside of the housing 120 and a heat dissipation plate 162 which is provided to the thermal conductor 161 to dissipate heat transmitted via the thermal conductor 161 to the outside. In more detail, the thermal conductor 161 may be a metal plate, a heat sink or the like. Further, not shown in the drawing, a cooling fan (not shown) for forced cooling may be provided to the heat dissipation plate 162.

Accordingly, the heat inside the housing 120 can be dissipated through the thermal conductor 161 and the heat dissipation plate 162.

In addition, the high intensity line-focused ultrasound generation device according to a first embodiment of the present invention, as shown in (b) of FIG. 9 and FIG. 10, may further include a first position detecting part 170 which detects the position of the line-focused ultrasound transducer 110.

For example, the first position detecting part 170 may include a magnetic body 171 which is provided to the line-focused ultrasound transducer 110 and a magnetic sensor 172 which is provided to the housing in correspondence with the magnetic body 171 to detect the position of the magnetic body 171. In particular, when the line-focused ultrasound transducer 110 is in an initial position, the initial positions of the magnetic body 171 and the magnetic sensor 172 may be determined with reference to the focusing point of the ultrasound generated by the line-focused ultrasound transducer 110. At this time, the magnetic sensor 172 can precisely sense without being interfered by the ultrasound transmitting material in the housing 120, when compared to an infrared ray sensor or the like.

Accordingly, since the initial position is determined by the first position detecting part 170, the precise position of the line-focused ultrasound transducer 110 can be detected from the moving distance of the first linear motor 131a.

Further, the high intensity line-focused ultrasound generation device according to a first embodiment of the present invention, as shown in (b) of FIG. 9 and FIG. 10, may further include a memory for counting times of the movement of the line-focused ultrasound transducer 110 through the first position detecting part 170. Accordingly, the times of the movement of the line-focused ultrasound transducer 110 can be notified to a user.

Further, the high intensity line-focused ultrasound generation device according to a first embodiment of the present invention, as shown in (b) of FIG. 9 and FIG. 10, may further include a controller 190 controls the movement distance and the movement times of the line-focused ultrasound transducer 110 through the first position detecting part 170 and the memory 180. Accordingly, if the movement times suitable for the size and degree of the treatment area is determined, the controller 190 sends a control signal to the first linear motor 131a for operating the first linear motor 131a by the determined movement times with reference to the precise initial position by the first position detecting part 170.

The magnetic sensor 172, the memory 180 and the controller 190 may be mounted on a printed circuit board 210 so as to be electrically connected to one another.

Further, the reference numeral 141 designates a lamp for showing an operation state, and the reference numeral 211 designates a connector which is electrically connected to a socket 142 of the grip 140.

Hereinafter, referring to FIG. 11, the high intensity line-focused ultrasound generation device according to a second embodiment of the present invention will be described.

FIG. 11 is a sectional view schematically showing a high intensity line-focused ultrasound generation device according to a second embodiment of the present invention.

The high intensity line-focused ultrasound generation device according to a second embodiment of the present invention, as shown in FIG. 11, is equal to the first embodiment of the present invention except the point that the length of a slider 2153 is changed and a second position detecting part 220 and a sealing part 225 are further provided, so explanation only for the length of the slider 2153 and the second position detecting part 220 and the sealing part 250 will be made. In addition, the same reference numeral will be used for the same element with the first embodiment of the present invention, and the explanations of the elements of FIG. 11 which are not designated by reference numerals refer to those of FIG. 9 and FIG. 10 and the explanation of the first embodiment of the present invention.

The length of the slider 2153 may be determined such that an end of the slider 2153 is located within the grip 140 with reference to the initial state in which the slider 2153 is completely pulled by the driving unit 130.

The second position detecting part 220 detects a position of the line-focused ultrasound transducer 110 in a similar way to the first position detecting part 170 of the first embodiment of the present invention.

For example, the second position detecting part 220 may include a first position hole 221 which is formed at a portion of the end of the slider 2153 which is disposed within the grip 140 with reference to the initial state in which the slider 2153 is completely pulled by the driving unit 130 and a proximate sensor 222 which is provided the grip 140 in correspondence with the first position hole 221 to detect the first position hole 221.

Accordingly, the first position sensing part 170 of the first embodiment of the present invention is realized as the magnetic sensor 172 in the housing which can be used in the ultrasound transmitting material, but the second position detecting part 220 is realized as the proximate sensor 222 in the grip 140 where there is no ultrasound transmitting material. In particular, since the second position detecting part 220 is disposed within the grip 140, it can precisely detect the position of the line-focused ultrasound transducer 110 without being interfered by the ultrasound transmitting material.

Further, in order to detect the position of the line-focused ultrasound transducer 110 more precisely, the first position detecting part 170 and the second position detecting part 220 can be used together.

Further, the second position hole 223 may be further formed at a portion of the other end of the slider 2153 which is disposed within the grip 140 such that the slider 2153 is detected by the proximate sensor 222 in case that it is unintentionally separated from the driving unit 130.

Further, an opening 224 for inserting and taking out the slider 2153 may be formed in the housing 120 and the grip 140, and a sealing part 225 for preventing the ultrasound transmitting material in the housing 120 from leaking to the grip 140 through the opening 224 may also be provided.

For example, the sealing part 225 may be realized as a sealing member 225a of a contractible bellows shape which encloses the slider 2153 and one end of which is provided to the opening 224 and the other end of which is provided to the support member 152 of the line-focused ultrasound transducer 110.

Hereinafter, referring to FIG. 12, the high intensity line-focused ultrasound generation device.

FIG. 12 is a sectional view schematically showing a high intensity line-focused ultrasound generation device according to a third embodiment of the present invention.

The high intensity line-focused ultrasound generation device according to a third embodiment of the present invention, as shown in FIG. 12, is equal to the first embodiment of the present invention except the point that an attaching member 240 is added to the therapeutic window 230, so explanation only for the therapeutic window 230 and the attaching member 240 will be made. In addition, the same reference numeral will be used for the same element with the first embodiment of the present invention, and the explanations of the elements of FIG. 12 which are not designated by reference numerals refer to those of FIG. 9 and FIG. 10 and the explanation of the first embodiment of the present invention.

The therapeutic window 230 plays a role of closing the first opening part 121 of the housing 120 and allowing the line-focused ultrasound to pass therethrough.

The attaching member 240 attaches the therapeutic window 230 to the first opening part 121, and for example may be an adhesive or a double-sided adhesive tape.

Hereinafter, referring to FIG. 13, the high intensity line-focused ultrasound generation device according to a fourth embodiment of the present invention will be described in detail.

FIG. 13 is a sectional view schematically showing a high intensity line-focused ultrasound generation device according to a fourth embodiment of the present invention.

The high intensity line-focused ultrasound generation device according to a fourth embodiment of the present invention, as shown in FIG. 13, is equal to the first embodiment of the present invention except the point that a temperature detecting part 250 is further provided, so explanation only for the temperature detecting part 250 will be made. In addition, the same reference numeral will be used for the same element with the first embodiment of the present invention, and the explanations of the elements of FIG. 13 which are not designated by reference numerals refer to those of FIG. 9 and FIG. 10 and the explanation of the first embodiment of the present invention.

The temperature detecting part 250 is provided to the housing 120 and plays a role of detecting the temperature inside of the housing 120.

For example, the temperature detecting part 250 may include a temperature detecting rod 251 which is disposed within the housing 120 and a temperature sensor 252 which is disposed outside the housing 120 and is connected to the temperature detecting rod 251 to detect the temperature of the temperature detecting rod 251.

In particular, the temperature sensor 252 may be mounted to the above-mentioned printed circuit board 210 to be electrically connected to the controller 190 of the like. Here, the controller 190 may control the cooling fan (not shown) to cool the housing 120 if the temperature detected by the temperature sensor 252 is higher than a predetermined temperature.

Hereinafter, referring to FIG. 14, the high intensity line-focused ultrasound generation device according to a fifth embodiment of the present invention will be described.

FIG. 14 is a sectional view schematically showing a high intensity line-focused ultrasound generation device according to a fifth embodiment of the present invention.

The high intensity line-focused ultrasound generation device according to a fifth embodiment of the present invention, as shown in FIG. 14, is equal to the first embodiment of the present invention except the point that the linear guiding part (150 of FIG. 9) has been cancelled and elements have been added to the driving unit 130, so explanation only for the driving unit 130 will be made. In addition, the same reference numeral will be used for the same element with the first embodiment of the present invention, and the explanations of the elements of FIG. 14 which are not designated by reference numerals refer to those of FIG. 9 and FIG. 10 and the explanation of the first embodiment of the present invention.

The driving unit 130 may further include a vertical guiding rail 133 which is provided to allow the support bracket 132 to which the first linear motor 131a described in the first embodiment is fixed to be able to vertically move and a second driving part 134 which moves the support bracket 132 vertically.

For example, the second driving part 134 may include a first rotation motor which is disposed outside the housing 120, a pinion 134b which is shaft-connected to the first rotation motor 134a, and a rack 134c which is provided to the support bracket 132 and is connected to the pinion 134 by a gear engagement.

Accordingly, the first linear motor 131a moves vertically along the guiding rail 133 by the driving of the first rotation motor 134a and the line-focused ultrasound transducer 110 which is provided thereto also moves vertically. During this process, the focused line of the line-focused ultrasound transducer 110 is precisely located on the treatment area.

Further, while the moving bar 131b moves in a forward/backward direction by the driving of the first linear motor 131a which is fixed to the support bracket 132, the line-focused ultrasound transducer 110 which is provided thereto also moves in a forward/backward direction. During this process, the line-focused ultrasound transducer 110 treats the treatment area.

Hereinafter, referring to FIG. 15, the high intensity line-focused ultrasound generation device according to a sixth embodiment of the present invention will be described.

FIG. 15 is a sectional view schematically showing a high intensity line-focused ultrasound generation device according to a sixth embodiment of the present invention.

The high intensity line-focused ultrasound generation device according to a sixth embodiment of the present invention, as shown in FIG. 15, is equal to the first embodiment of the present invention except the point that a coupling/decoupling unit 260 is added, so explanation only for the coupling/decoupling unit 260 will be made. In addition, the same reference numeral will be used for the same element with the first embodiment of the present invention, and the explanations of the elements of FIG. 15 which are not designated by reference numerals refer to those of FIG. 9 and FIG. 10 and the explanation of the first embodiment of the present invention.

The coupling/decoupling unit 260 is disposed between the line-focused ultrasound transducer 110 and the driving unit 130 and plays a role of coupling or decoupling the line-focused ultrasound transducer 110 to or from the driving unit 130.

For example, the coupling/decoupling unit 260 may include a first magnet 261 which is provided to the slider 153 of the line-focused ultrasound transducer 110 and a second magnet 262 which is provided to the driving unit 130 in correspondence with the first magnet 261 and applies an attractive force to the first magnet 261.

Accordingly, if the grip 140 is coupled to the housing 120, the slider 153 of the line-focused ultrasound transducer 110 and the moving bar 131*b* of the driving unit 130 are coupled by the attractive force between the first and the second magnets 261 and 262, and if the grip 140 is decoupled from the housing 120, the attractive force between the first and the second magnets 261 and 262 are cancelled by an external force so as to be separated from one another.

Hereinafter, referring to FIG. 16 and FIG. 17, the high intensity line-focused ultrasound generation device according to a seventh embodiment of the present invention will be described.

FIG. 16 is a sectional view schematically showing a high intensity line-focused ultrasound generation device according to a seventh embodiment of the present invention, wherein (a) is a sectional view and (b) is a sectional view of a grip which is separated from the housing.

FIG. 17 schematically shows a line-focused ultrasound transducer of a high intensity line-focused ultrasound generation device of FIG. 16.

The high intensity line-focused ultrasound generation device according to a seventh embodiment of the present invention, as shown in FIG. 16 and FIG. 17, is equal to the sixth embodiment of the present invention except the point that the shape of the support member 2152 of the line-focused ultrasound transducer 110 has been changed, an ultrasound transducer 280 for obtaining an image has been added, and accordingly the shapes of the housing 2120 and the grip 2140 have been changed, so explanation only for the supper member 2152 of the line-focused ultrasound transducer 110 and the ultrasound transducer 280 for obtaining an image 250 will be made. In addition, the same reference numeral will be used for the same element with the sixth embodiment of the present invention, and the explanations of the elements of FIG. 16 which are not designated by reference numerals refer to those of FIG. 15 and the explanation of the sixth embodiment of the present invention.

A second opening part 270 is further formed on the support member 2152 of the line-focused ultrasound transducer 110.

The ultrasound transducer 280 for obtaining an image is provided to the housing 2120 or the grip 2140 and is configured to obtain an image through the second opening part 270.

In particular, the ultrasound transducer 280 for obtaining an image may be provided to the grip 2140, and it may be decoupled when the grip 2140 is decoupled from the housing 2120 by the coupling/decoupling unit 260. Accordingly, when the line-focused ultrasound transducer 110, the housing 2120 or the like is replaced, the ultrasound transducer 280 for obtaining an image which is expensive may be remained in the grip 2140.

Hereinafter, referring to FIG. 18, the high intensity line-focused ultrasound generation device according to an eighth embodiment of the present invention will be described.

FIG. 18 schematically shows a high intensity line-focused ultrasound generation device according to an eighth embodiment of the present invention, where (a) is a sectional view seen from the front and (b) is a sectional view seen from the side.

The high intensity line-focused ultrasound generation device according to an eighth embodiment of the present invention, as shown in FIG. 18, is equal to the first embodiment of the present invention except the point that an laser oscillator 290 is added, so explanation only for the laser oscillator 290 will be made. In addition, the same reference numeral will be used for the same element with the first embodiment of the present invention, and the explanations of the elements of FIG. 18 which are not designated by reference numerals refer to those of FIG. 9 and FIG. 10 and the explanation of the first embodiment of the present invention.

The laser oscillators 290 may be respectively disposed at both sides of a front end of the grip 140 and at a rear end of the grip and oscillate lasers for position verification in a shape of a point or a line on the treatment area. Accordingly, the user can precisely recognize the treatment position of the treatment area.

Hereinafter, referring to FIG. 19, the high intensity line-focused ultrasound generation device according to a ninth embodiment of the present invention will be described.

FIG. 19 schematically shows a grip of a high intensity line-focused ultrasound generation device according to a ninth embodiment of the present invention, where (a) is a sectional view and (b) is a conceptual diagram of a heat exchanger which is provided to the grip.

The high intensity line-focused ultrasound generation device according to a ninth embodiment of the present invention, as shown in FIG. 19, is equal to the first embodiment of the present invention except the point that a second cooling part 310 has been added, so explanation only for the second cooling part 310 will be made. In addition, the same reference numeral will be used for the same element with the first embodiment of the present invention, and the explanations of the elements of FIG. 19 which are not designated by reference numerals refer to those of FIG. 9 and FIG. 10 and the explanation of the first embodiment of the present invention.

The second cooling part 310 is provided at a portion of the grip 140 which the housing (120 of FIG. 9) contacts and plays a role of cooling heat of the housing 120.

For example, the second cooling part 310 may include a heat transmitting plate 311 which is provided to the grip 140 and contacts the housing 120 and a heat exchanger 312 which contacts the heat transmitting plate 311 and exchanges heat of the heat transmitting plate 311 through circulation of cooling water therein. Accordingly, heat of the housing 120 can transfer to the heat exchanger 312 via the heat transmitting plate 311 so as to be cooled.

Further, in order to improve the cooling efficiency, a thermoelectric element 313 may be further disposed between the heat transmitting plate 311 and the heat exchanger 312.

Hereinafter, referring to FIG. 20, the high intensity line-focused ultrasound generation device according to a tenth embodiment of the present invention will be described.

FIG. 20 is a sectional view schematically showing a grip of a high intensity line-focused ultrasound device according to a tenth embodiment of the present invention.

The high intensity line-focused ultrasound generation device according to a tenth embodiment of the present invention, as shown in FIG. 20, is equal to the first embodiment of the present invention except the point that a second cooling part 2310 has been added, so explanation only for the second cooling part 2310 will be made. In addition, the same reference numeral will be used for the same element with the first embodiment of the present invention, and the explanations of the elements of FIG. 20 which are not designated by reference numerals refer to those of FIG. 9 and FIG. 10 and the explanation of the first embodiment of the present invention.

The second cooling part 2310 is provided to a portion of the grip 140 which the housing (120 of FIG. 9) contacts and plays a role of cooling heat of the housing 120.

In particular, the second cooling part 310 may include a heat transmitting plate 2311 which is provided to the grip 140 to be vertically movable and an elastic member 2312 which is provided between the heat transmitting plate 2311 and the grip 140 in a state of adhering to the housing 120.

Accordingly, if the housing 120 is coupled to the grip 140, the elastic member 2312 is compressed by the coupling force, so the heat dissipating plate (162 of FIG. 9) of the housing (120 of FIG. 9) and the heat transmitting plate 2311 of the grip 140 becomes close to one another.

Hereinafter, referring to FIG. 21, the high intensity line-focused ultrasound generation device according to an eleventh embodiment of the present invention will be described.

FIG. 21 is a sectional view schematically showing a high intensity line-focused ultrasound generation device according to an eleventh embodiment of the present invention.

The high intensity line-focused ultrasound generation device according to an eleventh embodiment of the present invention, as shown in FIG. 21, different from the first embodiment of the present invention, has a feature that a first linear motor 3131a is disposed above the housing 3120 by a fixing bracket 3132 apart from the housing 3120, a support member 3152 of the line-focused ultrasound transducer 110 penetrates an upper portion of the housing 3120 so as to be connected to the moving bar 3131b of the first linear motor 3131a, and a moving passageway 3121 for the support member 3152 is provided at an upper portion of the housing 3120.

Accordingly, if the first linear motor 3131a operates, the moving bar 3131b moves in a forward/backward direction, and the support member 3152 moves in a forward/backward direction along the moving passageway 3121. During this process, the line-focused ultrasound transducer 110 performs treatment of the treatment area.

Further, since the first linear motor 3131a can be disposed in a space above the housing 3120, it can be useful when there is a spatial limitation in a longitudinal direction of the device.

Hereinafter, referring to FIG. 22, the high intensity line-focused ultrasound generation device according to a twelfth embodiment of the present invention will be described.

FIG. 22 schematically shows a high intensity line-focused ultrasound generation device according to a twelfth embodiment of the present invention, where (a) is a sectional view seen from the side and (b) is a sectional view seen from the front.

The high intensity line-focused ultrasound generation device according to a twelfth embodiment of the present invention, as shown in FIG. 22, generates ultrasound which is focused in a line, and includes a housing 4120, a line-focused ultrasound transducer 110 and a driving unit 4130.

The housing 4120 may be filled with ultrasound transmitting material (not shown) and may have a sealed structure in order to prevent the ultrasound transmitting material from being leaked.

The line-focused ultrasound transducer 110 is provided to be movable within the housing 4120, and since the explanation thereof is equal to that of the line-focused ultrasound transducer according to the above-described embodiments, detailed description thereof will be omitted.

The driving unit 4130 plays a role of moving the line-focused ultrasound transducer 110. Hereinafter, referring to FIG. 22, the driving unit 4130 will be described in more detail.

The driving unit 4130 may include a rotating shaft 4131 to which the line-focused ultrasound transducer 110 is provided and is disposed in a lateral direction in the housing 4120 to form a rotation center of the line-focused ultrasound transducer 110 and a third driving part 4132 which is provided to the outside of the housing 4120 and applies rotation force to the line-focused ultrasound transducer 110 about the rotating shaft 4131.

For example, the third driving part 4132 may include a second rotation motor 4132a which is provided to the outside of the housing 4120, a first pulley 4132b which is shaft-coupled to the second rotation motor 4132a, a second pulley 4132d which is shaft-coupled to the rotating shaft 4131 and a connecting belt 4132c which connects the first and the second pulleys 4132b and 4132d.

Accordingly, the first pulley 4132b rotates by the second rotation motor 4132a, and at the same time the second pulley 4132d rotates which is connected to the first pulley 4132b by the connection belt 4132c, so the line-focused ultrasound transducer 110 rotates in a clockwise or a counter clockwise about the rotating shaft 4131. During this rotation, the line-focused ultrasound transducer 110 performs the treatment for the treatment area.

Hereinafter, referring to FIG. 23, the high intensity line-focused ultrasound generation device according to a thirteenth embodiment of the present invention will be described.

FIG. 23 schematically shows a high intensity line-focused ultrasound generation device according to a thirteenth embodiment of the present invention, where (a) is a sectional view seen from the side and (b) is a sectional view seen from the front.

The high intensity line-focused ultrasound generation device according to a thirteenth embodiment of the present invention, as shown in FIG. 23, generates ultrasound which is focused in a line, and includes a housing 5120, a line-focused ultrasound transducer 110 and a driving unit 5130.

The housing 5120 may be filled with ultrasound transmitting material (not shown) and may have a sealed structure in order to prevent the ultrasound transmitting material from being leaked.

The line-focused ultrasound transducer 110 is provided to be movable within the housing 5120, and since the explanation thereof is equal to that of the line-focused ultrasound transducer according to the above-described embodiments, detailed description thereof will be omitted.

The driving unit 5130 plays a role of moving the line-focused ultrasound transducer 110. Hereinafter, referring to FIG. 23, the driving unit 5130 will be described in more detail.

The driving unit 5130 may include a rotating shaft 5131 to which the line-focused ultrasound transducer 110 is provided and is disposed in a lateral direction in the housing 5120 to form a rotation center of the line-focused ultrasound transducer 110 and a third driving part 5132 which is provided to the outside of the housing 5120 and applies rotation force to the line-focused ultrasound transducer 110 about the rotating shaft 5131.

In particular, the third driving part 5132 may include a third rotation motor 5132a which is provided to the outside of the housing 5120 and is shaft-coupled to the rotation shaft 5131 and a support bearing 5132b which is provided to the housing 5120 and supports a motor shaft of the third rotation motor 5132a to be rotatable.

Accordingly, if the motor shaft rotates by the driving of the third rotation motor 5132a, the line-focused ultrasound transducer 110 which is directly connected thereto rotates in a clockwise or a counter clockwise about the rotating shaft 5131. During this rotation, the line-focused ultrasound transducer 110 performs the treatment for the treatment area.

Hereinafter, referring to FIG. 24, the high intensity line-focused ultrasound generation device according to a fourteenth embodiment of the present invention will be described.

FIG. 24 is a sectional view schematically showing a high intensity line-focused ultrasound generation device according to a fourteenth embodiment of the present invention.

The high intensity line-focused ultrasound generation device according to a fourteenth embodiment of the present invention, as shown in FIG. 24, generates ultrasound which is focused in a line, and includes a housing 6120, a line-focused ultrasound transducer 110 and a driving unit 6130.

The housing 6120 may be filled with ultrasound transmitting material (not shown) and may have a sealed structure in order to prevent the ultrasound transmitting material from being leaked.

The line-focused ultrasound transducer 110 is provided to be movable within the housing 6120, and since the explanation thereof is equal to that of the line-focused ultrasound transducer according to the above-described embodiments, detailed description thereof will be omitted.

The driving unit 6130 plays a role of moving the line-focused ultrasound transducer 110. Hereinafter, referring to FIG. 24, the driving unit 6130 will be described in more detail.

The driving unit 6130 may include a rotating shaft 6131 to which the line-focused ultrasound transducer 110 is provided and is disposed in a lateral direction in the housing 6120 to form a rotation center of the line-focused ultrasound transducer 110 and a third driving part 6132 which is provided to the outside of the housing 6120 and applies rotation force to the line-focused ultrasound transducer 110 about the rotating shaft 6131.

In particular, the third driving part 6132 may include a fourth rotation motor 6132a which is provided to the outside of the housing 6120, a first pressing protrude 6132b which is provided to the rotation shaft 6131 and a power transmitting member 6132c one end of which is rotatably connected to an end of the first pressing protrude 6132b and the other end of which is shaft-coupled to the fourth rotation motor 6132a so as to transmit the rotation force of the fourth rotation motor 6132a to the rotating shaft 6131 together with the first pressing protrude 6132b.

Accordingly, if the motor shaft rotates by the driving of the fourth rotation motor 6132a, the power transmitted to the power transmitting member 6132c moves the end of the first pressing protrude 6132b in a circumferential direction, so the line-focused ultrasound transducer 110 which is provided thereto rotates in a clockwise or a counter clockwise about the rotating shaft 6131. During this rotation, the line-focused ultrasound transducer 110 performs the treatment for the treatment area. Meanwhile, reference numeral 6133 designates a proximate sensor which detects the amount of rotation.

Hereinafter, referring to FIG. 25, the high intensity line-focused ultrasound generation device according to a fifteenth embodiment of the present invention will be described.

FIG. 25 is a sectional view schematically showing a high intensity line-focused ultrasound generation device according to a fifteenth embodiment of the present invention.

The high intensity line-focused ultrasound generation device according to a fifteenth embodiment of the present invention, as shown in FIG. 25, generates ultrasound which is focused in a line, and includes a housing 7120, a line-focused ultrasound transducer 110 and a driving unit 7130.

The housing 7120 may be filled with ultrasound transmitting material (not shown) and may have a sealed structure in order to prevent the ultrasound transmitting material from being leaked.

The line-focused ultrasound transducer 110 is provided to be movable within the housing 7120, and since the explanation thereof is equal to that of the line-focused ultrasound transducer according to the above-described embodiments, detailed description thereof will be omitted.

The driving unit 7130 plays a role of moving the line-focused ultrasound transducer 110. Hereinafter, referring to FIG. 25, the driving unit 7130 will be described in more detail.

The driving unit 7130 may include a rotating shaft 7131 to which the line-focused ultrasound transducer 110 is provided and is disposed in a lateral direction in the housing 7120 to form a rotation center of the line-focused ultrasound transducer 110 and a third driving part 7132 which is provided to the outside of the housing 7120 and applies rotation force to the line-focused ultrasound transducer 110 about the rotating shaft 7131.

In particular, the third driving part 7132 may include a second linear motor 7132a which is provided to the outside of the housing 7120, a moving bar 7132b which moves in a forward/backward direction by the second linear motor 7132a and a second pressing protrude 7132c one end of which is provided to the rotating shaft 7131 and the other end of which is rotatably connected to the moving bar 7132b.

In addition, the third driving part 7132 may include a hinge pin 7132d which connects the moving bar 7132b to the second pressing protrude 7132c to be rotatable and a hinge hole 7132e which is formed at an end of the second pressing protrude 7132c and to which the hinge pin 7132d is inserted.

In particular, the hinge hole 7132*e* may be formed to be extended in a longitudinal direction of the pressing protrude 7132*c*, such that the moving bar 7132*b* moves smoothly in a forward/backward direction while the other end of the second pressing protrude 7132*c* moves in a circumferential direction about the rotating shaft 7131.

Accordingly, while the moving bar 7132*b* moves in a forward/backward direction by the driving of the second linear motor 7132*a*, an end of the second pressing protrude 7132*c* which is hingedly connected thereto moves along a circumferential direction, so the line-focused ultrasound transducer 110 which is provided thereto rotates in a clockwise or a counter clockwise about the rotating shaft 7131. During this rotation, the line-focused ultrasound transducer 110 performs the treatment for the treatment area. Meanwhile, reference numeral 7133 designates a proximate sensor which detects the amount of rotation.

As described above, the line-focused ultrasound transducer and the high intensity line-focused ultrasound generation device including the same according to the embodiments of the present invention have the following effects.

According to the embodiments of the present invention, since ultrasound is focused in a line due to the therapeutic piezoelectric member having the hollow semi-cylindrical shape, time for treatment can be reduced and treatment effect can be maximized, compared to the device in which ultrasound is focused on one point.

In addition, according to the embodiments of the present invention, since the ultrasound transducer automatically moves in a housing by a driving unit, the focusing point of the ultrasound transducer can automatically move on a plurality of target sheets or on a long target sheet (e.g., treatment area), without a user's effort to move the housing.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention relates to an ultrasound transducer and a high intensity line-focused ultrasound generation device including the same, so it can be applicable to a medical device or the like so that it has an industrial applicability.

The invention claimed is:

1. A high intensity line-focused ultrasound generation device which focuses in a line shape comprising:
   a housing which is filled with an ultrasound transmitting material;
   a line-focused ultrasound transducer which is provided within the housing to be movable;
   a driving unit moving the line-focused ultrasound transducer;
   a grip which is provided to the housing to be able to be coupled and decoupled; and
   a slider one end of which is connected to the line-focused ultrasound transducer and the other end of which is connected to the driving unit to be able to be coupled and decoupled; and
   a position detecting part which detects a position of the line-focused ultrasound transducer,
   wherein the position detecting part comprises:
   a first position hole which is formed at a portion of an end of the slider which is disposed within the grip with reference to an initial state in which the slider is completely pulled by the driving unit;
   a proximate sensor which is provided to the grip in correspondence with the first position hole to detect the first position hole; and
   a second position hole which is formed at a portion of the other end of the slider which is disposed within the grip such that the slider is detected by the proximate sensor in case that the slider is unintentionally separated from the driving unit.

2. A high intensity line-focused ultrasound generation device which focuses in a line shape comprising:
   a housing which is filled with an ultrasound transmitting material;
   a line-focused ultrasound transducer which is provided within the housing to be movable;
   a driving unit moving the line-focused ultrasound transducer;
   a grip which is provided to the housing to be able to be coupled and decoupled;
   an opening part which is formed to the line-focused ultrasound transducer; and
   an ultrasound transducer for obtaining an image which is provided to the housing or the grip and obtains an image through the opening part.

3. The high intensity line-focused ultrasound generation device of claim 2, wherein the ultrasound transducer for obtaining an image is provided to the grip and is formed to be separated together when the grip is separated from the housing.

4. A high intensity line-focused ultrasound generation device which focuses in a line shape comprising:
   a housing which is filled with an ultrasound transmitting material;
   a line-focused ultrasound transducer which is provided within the housing to be movable; and
   a driving unit moving the line-focused ultrasound transducer,
   wherein the driving unit comprises:
   a rotating shaft to which the line-focused ultrasound transducer is provided and is disposed in a lateral direction in the housing to form a rotation center of the line-focused ultrasound transducer; and
   a driving part which is provided to the outside of the housing and applies rotation force to the line-focused ultrasound transducer about the rotating shaft, and
   wherein the driving part comprises:
   a linear motor which is provided to the outside of the housing;
   a moving bar which moves in a forward/backward direction by the linear motor; and
   a pressing protrude one end of which is provided to the rotating shaft and the other end of which is rotatably connected to the moving bar.

5. The high intensity line-focused ultrasound generation device of claim 4, wherein the driving part further comprises:
   a hinge pin which connects the moving bar to the pressing protrude to be rotatable; and
   a hinge hole which is formed at an end of the pressing protrude and to which the hinge pin is inserted,
   wherein the hinge hole is formed to be extended in a longitudinal direction of the pressing protrude such that the moving bar moves smoothly in a forward/backward direction while the other end of the pressing protrude moves in a circumferential direction about the rotating shaft.

\* \* \* \* \*